(12) United States Patent
Drysdale et al.

(10) Patent No.: US 10,146,912 B2
(45) Date of Patent: Dec. 4, 2018

(54) MEDICAL APPARATUS

(75) Inventors: Ian George Moir Drysdale, Inverness (GB); David Morris Williams, Wirral (GB)

(73) Assignee: DanMedical Ltd. (GB)

( * ) Notice: Subject to any disclaimer, the term of this patent is extended or adjusted under 35 U.S.C. 154(b) by 456 days.

(21) Appl. No.: 13/259,908

(22) PCT Filed: Mar. 26, 2010

(86) PCT No.: PCT/GB2010/000564
§ 371 (c)(1),
(2), (4) Date: Dec. 19, 2011

(87) PCT Pub. No.: WO2010/112815
PCT Pub. Date: Oct. 7, 2010

(65) Prior Publication Data
US 2012/0108911 A1    May 3, 2012

(30) Foreign Application Priority Data
Mar. 30, 2009 (GB) .................................. 0905377.8

(51) Int. Cl.
*G06F 3/00* (2006.01)
*G06F 19/00* (2018.01)

(52) U.S. Cl.
CPC .......... *G06F 19/3418* (2013.01); *G06F 19/00* (2013.01)

(58) Field of Classification Search
None
See application file for complete search history.

(56) References Cited

U.S. PATENT DOCUMENTS 4,051,355 A * 9/1977 Lin ..................... G06F 11/1008
                                                    365/200
4,748,562 A   5/1988 Miller et al.
(Continued)

FOREIGN PATENT DOCUMENTS

EP      0059172      9/1982
EP      0978255      2/2000
(Continued)

*Primary Examiner* — Hyun Nam
*Assistant Examiner* — Dean Phan
(74) *Attorney, Agent, or Firm* — Plumsea Law Group, LLC

(57) ABSTRACT

The present invention relates to medical apparatus for monitoring one or more physiological conditions of a patient and a method for monitoring one or more physiological conditions of a patient. Apparatus for measuring medical data is described, comprising: at least one medical data gathering module, at least one microprocessor, and further wherein the apparatus further comprises a medical data handling module separate from the at least one microprocessor for buffering medical data transfer between the medical data gathering module and the microprocessor and optionally further wherein the medical data handling module can gather and store data in predetermined groups of data and the microprocessor can retrieve data from the medical data handling module in one or more multiples of predetermined groups of data. A method for measuring medical data is described, comprising: providing at least one medical data gathering module; providing at least one microprocessor; providing a data handling module separate from the at least one microprocessor; buffering medical data transfer between the medical data gathering module and the microprocessor optionally by gathering and storing data in predetermined groups of data and retrieving data from the medical data handling module in one or more multiples of predetermined groups of data.

24 Claims, 23 Drawing Sheets

(56) References Cited

U.S. PATENT DOCUMENTS

| | | | |
|---|---|---|---|
| 4,920,489 A * | 4/1990 | Hubelbank et al. | 600/519 |
| 4,924,875 A * | 5/1990 | Chamoun | A61B 5/0452 128/908 |
| 5,228,450 A * | 7/1993 | Sellers | 600/524 |
| 5,377,687 A | 1/1995 | Evans et al. | |
| 5,417,222 A | 5/1995 | Dempsey et al. | |
| 5,687,717 A * | 11/1997 | Halpern | A61B 5/0205 128/903 |
| 5,701,894 A | 12/1997 | Cherry et al. | |
| 5,792,065 A * | 8/1998 | Xue et al. | 600/516 |
| 5,891,046 A * | 4/1999 | Cyrus et al. | 600/510 |
| 6,256,531 B1 * | 7/2001 | Ilmoniemi et al. | 600/544 |
| 6,454,708 B1 | 9/2002 | Ferguson et al. | |
| 6,948,110 B2 * | 9/2005 | Koishi | 714/752 |
| 2002/0007198 A1 * | 1/2002 | Haupert | A61N 1/37 607/30 |
| 2002/0123672 A1 * | 9/2002 | Christophersom | A61N 1/37282 600/300 |
| 2004/0243015 A1 * | 12/2004 | Smith | A61B 5/0011 600/511 |
| 2005/0108055 A1 * | 5/2005 | Ott et al. | 705/2 |
| 2006/0009697 A1 | 1/2006 | Banet et al. | |
| 2006/0178706 A1 * | 8/2006 | Lisogurski et al. | 607/10 |
| 2006/0229521 A1 * | 10/2006 | Barr | 600/509 |
| 2007/0213622 A1 | 9/2007 | Reisfeld | |
| 2008/0058614 A1 | 3/2008 | Banet et al. | |
| 2008/0154099 A1 * | 6/2008 | Aspel | G06F 19/3418 600/301 |
| 2009/0006034 A1 | 1/2009 | Hayter et al. | |
| 2010/0010433 A1 * | 1/2010 | Krogh | G06F 19/3456 604/66 |
| 2010/0022882 A1 * | 1/2010 | Duckworth | A61B 5/6805 600/447 |

FOREIGN PATENT DOCUMENTS

| | | |
|---|---|---|
| EP | 1127538 | 8/2001 |
| WO | 9916351 | 4/1994 |
| WO | 9830145 | 7/1998 |
| WO | 2000051677 | 9/2000 |
| WO | 0062664 | 10/2000 |
| WO | 0230277 | 4/2002 |
| WO | 2005018447 | 3/2005 |

* cited by examiner

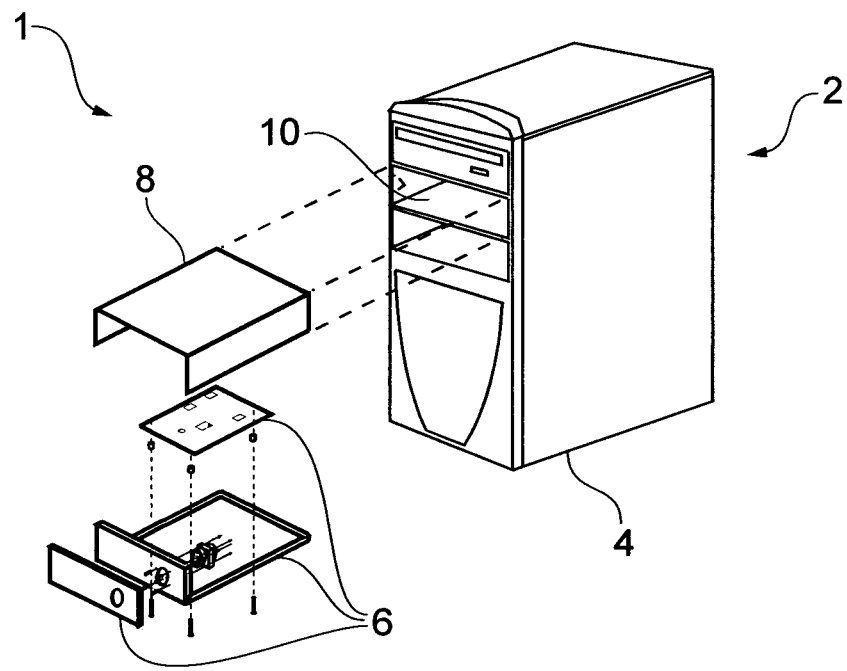
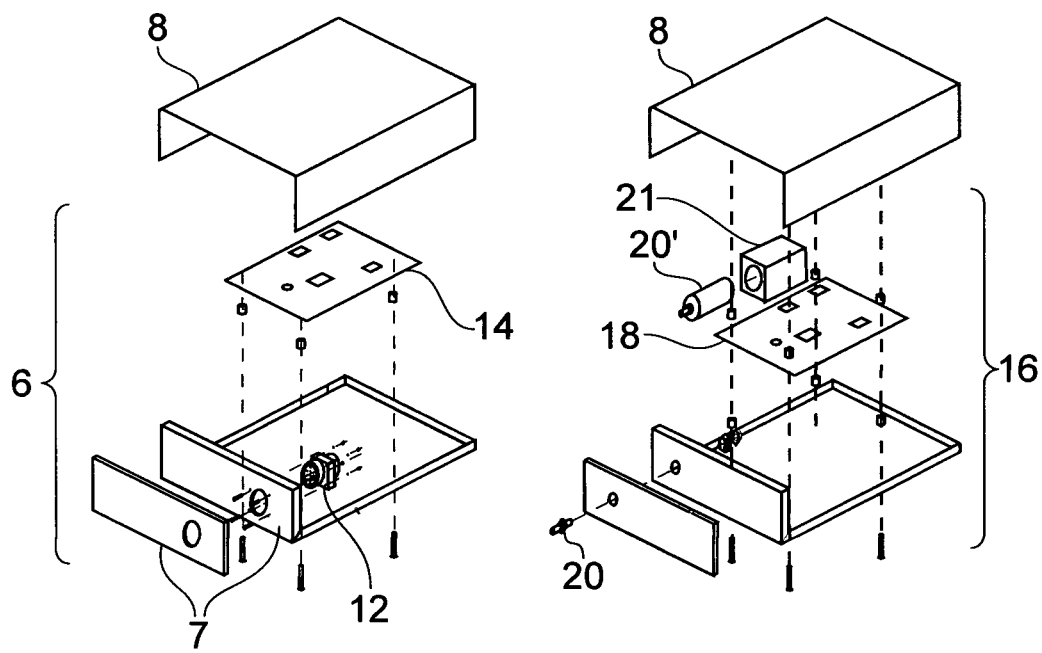
FIG. 1
FIG. 2
FIG. 3

54 Byte FPGA buffer includes data relating to ECG, skin temperature and BP

1. Lead Discriminator
2. LEAD 1
3. LEAD 1 Lead Off
4. LEAD 2
5. LEAD 2 Lead Off
6. LEAD 3
7. LEAD 3 Lead Off
8. AVF
9. AVR
10. AVL
11. C1
12. C1 Lead Off
13. C2
14. C2 Lead Off
15. C3
16. C3 Lead Off
17. C4
18. C4 Lead Off
19. C5
20. C5 Lead Off
21. C6
22. C6 Lead Off
23. Temperature connected
24. Temperature signal
25. Lead Discriminator
26. LEAD 1
27. LEAD 1 Lead Off
28. LEAD 2
29. LEAD 2 Lead Off
30. LEAD 3
31. LEAD 3 Lead Off
32. AVF
33. AVR
34. AVL
35. C1
36. C1 Lead Off
37. C2
38. C2 Lead Off
39. C3
40. C3 Lead Off
41. C4
42. C4 Lead Off
43. C5
44. C5 Lead Off
45. C6
46. C6 Lead Off
47. Temperature connected
48. Temperature signal
49- BP control
50- BP reading
51- VBatt
52- Volt_5V
53- Volt_min5V
54- Volt_3V3

FIG. 28

MEDICAL APPARATUS

FIELD OF THE INVENTION

The present invention relates to medical apparatus for monitoring one or more physiological conditions of a patient and a method for monitoring one or more physiological conditions of a patient.

BACKGROUND OF THE INVENTION

In medical devices, such as patient monitors, physiological measurements may be performed in which a cable is attached directly to a patent at one end by electrode wires to perform physiological tests, such as an electrocardiogram (ECG). A common design used to perform ECG measurements, consists of a number of electrode patches connected to the patient's skin in which voltage variations are recorded over a period of time, and the resulting signals are processed, stored and interpreted. The electrical signals sensed by the electrodes are commonly amplified and filtered in order to generate useful data. Although there are systems in the prior art for monitoring the physiological condition of a patient many of these prior art systems require a patient to wear a type of body monitor which then sends signals to a computer device such as a pda or a laptop. Example prior art systems are described in US 2006/009697, US 2008/058614, U.S. Pat. No. 5,417,222 WO2002/30277, WO98/30145, US2007/0213622, U.S. Pat. No. 5,377,687, EP0059172, US2008/0058614, WO2005/018447, WO99/16351, EP1127538 and WO2000/51677.

Certain prior art devices provide a computer print out or alternatively connect to third party computers. This limits the uses of such devices. Furthermore, a number of patents describe physiological monitors including portable ECG monitors such as U.S. Pat. No. 5,701,894 which describes an ambulatory physiological recorder that includes multiple selective plug-and-play signal input conditioners, a microprocessor system and operating and analysing software, and a removable memory module for data storage. In U.S. Pat. No. 6,454,708 there is described a system for monitoring health parameters and capturing data from a subject. The system includes a cordless sensor band with sensors for measuring full waveform ECG, full waveform respiration, skin temperature, and motion, and a connector which accepts a memory card or a smart card for storage of measured data.

Prior art devices are limited because:

1. Although cordless and wireless sensor bands and other prior art devices can give a full waveform ECG they do not always give a full 12 lead diagnostic quality ECG recording as required by a qualified medic.

2. Cordless and wireless sensor bands have inherent problems regarding battery and power usage e.g. potentially, at the critical moment, the battery runs out.

3. Cordless and wireless sensor bands have inherent problems regarding bandwidth e.g. potentially, at the critical moment, there is data loss.

4. Prior art devices are not fully integrated to or with a computer or a computer network e.g. patient data management becomes problematic with data loss and/or loss of resolution and/or integrity, and/or minimal or poor computing functionality.

5. Furthermore, these devices are not fully integrated with or into a computer or a computer network and in those cases, where data is transferred onto a memory card, this can be problematic for real time remote viewing by a health care professional (HCP).

Existing ECG devices used currently by the health care system do not lend themselves to portability and are kept in the surgery or health centre. These are also usually trolley mounted devices which merely produce a printed report which has to be scanned in or faxed to a specialist, resulting in low quality reports. This type of paper system also generates a patient confidentially problem for a user, where the patient details are exposed.

There is therefore a need in the art to provide a medical apparatus which: 1) is fully integrated to or within a computer system or a computer network 2) optionally, complies with regulatory safety standards for medical equipment 3) optionally, provides clinical grade resolution recordings, 4) optionally, provides the bandwidth facility to monitor a patient in real time 5) optionally, provides the facility to monitor a patient remotely, 6) optionally, has minimal computational impact on a computer it is integrated with.

Furthermore, prior art medical data gathering devices e.g. electrocardiogram (ECG) measurement devices do not provide the functionality of a computer with a standard operating system and standard programs such as Microsoft Word®, Microsoft Outlook®. This functionality is often missed by health care professionals in their day to day activities, especially now that patient data records are being centralized or where these are being reviewed remotely. It is an object of at least one aspect of the present invention to obviate or mitigate at least one or more of the aforementioned problems. It is a further object of at least one example embodiment of the present invention to provide improved medical apparatus which is capable of measuring data relating to a physiological condition of a patient and directly transmitting collected information to a computer. It is a further object of at least one aspect of the invention to provide improved medical apparatus.

SUMMARY OF THE INVENTION

In a first aspect of the invention there is provided apparatus for measuring medical data comprising: at least one medical data gathering module, at least one microprocessor, in which the apparatus further comprises a medical data handling module separate from the at least one microprocessor for buffering the transfer of medical data between the medical data gathering module and the at least one microprocessor.

Optionally, the medical data handling module is arranged to gather and store data in at least one predetermined group of data and the at least one microprocessor is arranged to retrieve data from the medical data handling module in one or more multiples of the at least one predetermined group of data. Optionally, the predetermined group of data is N bits of data and/or, optionally, T1 seconds worth of data. Optionally, the medical data handling module is arranged to gather N bits of data every T1 seconds from the least one medical data gathering module and store the sampled bits of data in the predetermined group of data. Optionally, 1/T1 is the rate that the medical data handling module samples data from the at least one medical data gathering module. Optionally, one or more multiples of the predetermined groups of data comprises one or more multiples of T1 seconds worth of data, and/or one or more multiples of N bits of data. Optionally, N equals 24 to 54, 24, 48, 54, 56 or any multiple thereof. Optionally, gathered medical data is stored and retrieved by the at least one microprocessor intermittently from the at least one medical data handling module.

Optionally, the microprocessor is a personal computer microprocessor or a laptop microprocessor and/or the microprocessor comprises Microsoft Windows® or Apple Mac® or Linux operating systems and/or, optionally, the apparatus comprises a computer comprising the at least one microprocessor. Optionally, the at least one medical data gathering module, the at least one microprocessor and the medical data handling module are located within a unitary housing or, optionally, within a unitary personal computer housing or, optionally, within a unitary laptop computer housing, Optionally, either 1) the at least one medical data gathering module, at least one microprocessor and the medical data handling module are co-located within a first housing, or, optionally, 2) the at least one medical data gathering module and data handling module are co-located in a first housing and the least one microprocessor is located within a second housing and communication means are provided to enable the medical data handling module and at least one microprocessor to communicate via wire and/or wirelessly, or, optionally, 3) the at least one medical data gathering module is located within a first housing and the at least one medical data handling module and at least one microprocessor are co-located within a second housing and communication means are provided to enable at least one medical data gathering module and at least one medical data handling module to communicate via wire and/or wirelessly. Optionally, where a wireless connection is provided this may be any one or more wireless connections standards such as infrared, WIFI, Bluetooth, 3G, satellite capability and so on.

Optionally, the housing, or first housing where first and second housings are provided, comprises at least one socket for connecting at least one medical data gathering module(s) to at least one medical data gathering connecting cable. Optionally, 1) a first housing for the at least one medical data gathering module is provided and a second housing for the microprocessor is provided and the first and second housing are adapted so that the first housing can sit beneath the second housing or vice versa; and/or, optionally, 2) an outer periphery of the first housing substantially matches an outer periphery of the second housing or vice versa; and, in either case, the medical data handling module is located within the first housing or the second housing. Optionally, the apparatus further comprises a cable identifying circuit for identifying the at least one medical data gathering cable connected thereto and/or, when the at least one medical data gathering module comprises an electrocardiogram data gathering module, for identifying whether a three lead or 10 lead electrocardiogram connecting cable is connected and/or, optionally, whether no ECG cable is connected.

Optionally, the medical data handling module comprises either 1) a further microprocessor or, optionally, 2) a further microprocessor and memory or, optionally, 3) system programmable on a chip or, optionally, 4) a field programmable gate array (FPGA). Optionally, the medical data handling module comprises at least one first in first out (FIFO) memory buffer. Optionally, the medical data handling module comprises a field programmable gate array and the field programmable gate array comprises a first in first out (FIFO) buffer. Optionally, the medical data handling module comprises either, 1) a programmable read only memory, or, optionally, 2) an erasable programmable read-only memory (EPROM), or, optionally, 3) an electronically erasable programmable read only memory (EEPROM), for delivering instructions to the medical data handling module. Optionally an EEPROM is used such as a Serial Flash Memory (SFM) to hold the FPGA program.

Optionally, the at least one data gathering module comprises one or more of an electrocardiogram data gathering module, an invasive or non-invasive blood pressure (BP) monitoring data gathering module; spirometry (lung function) data gathering module; pulse oximetry data gathering module; temperature data gathering module; both invasive and non-invasive blood pressure (BP) data gathering module; audiometry testing data gathering module; retinal testing data gathering module; ultrasound data gathering module; dermatology screening (image capture) data gathering module; imaging, tissue and/or wound care data gathering module; video endoscopy data gathering module; video conferencing data gathering module e.g. for live remote consultations; video and/or image capture data gathering module e.g. for remote consultations that may or may not be live; audio for detection of heart and/or lung sounds data gathering module; scaliometer (height) data gathering module; foetal heart Doppler ultrasound and/or audio acquisition and/or analysis data gathering module; and weighing scales data gathering module. Optionally, an electrocardiogram (ECG) data gathering module and/or a blood pressure (BP) data gathering module are provided. Optionally, simultaneous video conferencing functionality is provided e.g. for live consultations. This may be combined with live video/image medical data capture functionality for forwarding medical video/images during a video conference.

As will be appreciated by those skilled in the art, optionally, in addition to any one or more of the above mentioned data gathering modules being provided for interface with a microprocessor via a medical data handling module, one or more of the above medical data gathering modules may also be provided for connection directly to the at least one microprocessor, for example, via an internal data bus, such as an internal USB data bus which may have plug and play functionality. Typically, the apparatus is arranged so that data from at least one medical data gathering module is buffered by the medical data handling module. Optionally this may be one or both of an ECG data gathering module and a BP data gathering module. Optionally in addition, one or more further medical data gathering modules is provided connected to an internal data bus of the apparatus so as to deliver data to the at least one microprocessor directly (such as spirometer head 46 in FIG. 9). It will be appreciated by those skilled in the art that additional medical data gathering functionality can be added using medical data gathering modules connected to the internal data bus of a computer using for example a USB plug and play port, and by modification and/or upgrading and/or expanding the medical data processing software in the microprocessor.

Whilst it is preferred in one aspect of the invention for at least one medical data gathering module and at least one medical data handling module for buffering data therefrom to at least one microprocessor to be provided, in another separate aspect of the invention, the medical apparatus may comprise at least one microprocessor, and at least one internal data bus, and at least one medical data gathering module adapted for connection to the internal data bus, for example via a USB or other plug and play connector.

Optionally, in one example embodiment of either aspect, the apparatus comprises at least one medical data gathering module, at least one medical data handling module for buffering data therefrom to at least one microprocessor, at least one internal data bus, and at least further one medical data gathering module adapted for connection to the internal data bus, for example, via a USB or other plug and play connector.

Optionally, the medical data handling module is connected to at least one microprocessor of the personal computer or laptop computer, optionally, using an internal serial bus or an internal universal serial bus (USB). Optionally, the apparatus further comprises a revision controlled motherboard for hosting the at least one microprocessor. Optionally, a medical grade power supply is provided, optionally within a housing where one is provided, optionally, to power the at least one medical data gathering module, optionally, the at least one microprocessor and, optionally, the data handling module.

Optionally, the apparatus further comprises a medical data gathering cable lead off circuit for identifying when a medical data gathering cable has become disconnected from a patient, and/or, optionally, the apparatus further comprises a medical data gathering cable.

Optionally, the microprocessor comprises a medical data request retrieval module to request data retrieval from the medical data handling module. Optionally, the at least one medical data gathering module gathers data quasi-continuously, and/or, optionally, at a regular intervals and/or, optionally, the at least one microprocessor retrieves data intermittently and/or, optionally, or the at least one microprocessor retrieves data intermittently, optionally, either at regular or irregular intervals. Optionally, the medical data handling module samples data from the at least one medical data gathering module across N channels once every T1 seconds. Optionally, T1 is in the range 0.25 ms (millisecond) to 5 ms, or 0.5 ms to 2.5 ms, or T1 is 0.5 ms, 1 ms, 2 ms or 5 ms. Optionally, the least one microprocessor attempts to retrieve data in multiples of N from the data handling module once every T2 seconds, and/or, optionally, the at least one microprocessor may comprise medical data request retrieval module to retrieve data in multiples of N from the data handling module once every T2 seconds. Optionally, when the at least one microprocessor misses retrieving data either, optionally, 1) the at least one microprocessor attempts to retrieve data in multiples of N from the data handling module at another time and/or at the end of the next T2 second interval, and/or, optionally, 2) the at least one microprocessor comprises medical data retrieval module to retrieve data in multiples of N from the data handling module at another time and/or, optionally, at the end of the next T2 second interval. Optionally, a medical data gathering rate of sampling once every T1 seconds is the same as a medical data retrieval request rate of once every T2 seconds i.e. T1 equals T2. Optionally, a medical data retrieval transfer rate is Q×N bits per T2 seconds where Q is the number of sampling rounds of data to be retrieved and/or the medical data retrieval rate is up to the data transfer rate of an internal communications bus of the medical apparatus. Optionally, data in excess of a multiple of N and/or, optionally, in excess of a multiple of T1 seconds worth of data, is left in the medical data handling module until the next retrieval round. Optionally, analysis and calculation means is provided for use by the microprocessor to conduct analysis and calculation on the medical data at a resolution of T1 seconds, the resolution of the medical data gathering rate. Optionally, drawing and display means, and optionally a display, are provided for use by the microprocessor to draw every Mth data value to a display.

In a further aspect of the invention there is provided a method for measuring medical data, comprising: providing at least one medical data gathering module; providing at least one microprocessor; providing a medical data handling module separate from the at least one microprocessor; buffering medical data transfer between the medical data gathering module and the microprocessor the medical data handling module. Optionally, the method comprises gathering and storing data in predetermined groups of data in the medical data handling module and retrieving data from the medical data handling module in one or more multiples of the predetermined groups of data. Optionally, the method comprises sampling N data bits every T1 seconds, optionally, storing N data bits in memory every T1 seconds, optionally, reading N or, optionally, a multiple of N data bits every T2 seconds, optionally, emptying the memory of multiples of N data, optionally, leaving any fragments of multiples of data until following data collection round. Optionally, T1 equals T2, and/or, optionally, data retrieval transfer rate is Q×N bits per T2 seconds where Q the number of sampling rounds of data to be gathered.

According to a further aspect of the invention there is provided apparatus comprising a cable and a computer, said cable comprising: at least one lead capable of connecting the cable to a computer; and at least one further lead comprising medical components capable of detecting a physiological condition of a patient and the computer comprising cable connections components so that the cable is capable of detecting and transmitting information relating to the physiological condition of the patient to the computer. In this aspect, the invention therefore relates to a cable capable of providing a direct connection between medical components (e.g. ECG electrodes) capable of measuring and/or detecting a physiological condition of a patient and then transmitting collected information to the computer.

In particular embodiments, the medical components may therefore comprise a physiological measurement electronic circuit which may then transmit the detected and/or measured information. There may be at least one or a plurality of leads capable of connecting the at least one or a plurality of cables to the computer. At the end of at least one of the leads there may be an end socket which may comprise a series of pins which are capable of attaching the cable directly to a computer. The pins may insert into a suitable receiving socket in the computer. Typically, the receiving socket may be within a wall of a housing of the computer. There may be one or a plurality of leads capable of connecting the cable to medical components. The medical components such as electrodes may be used to detect at least one or a plurality of physiological conditions of the patient by measuring, for example, vital signals from a patient.

The electrodes may be attached to a patient's head, limbs and/or the chest area.

Optionally, the invention may comprise: an identifying mechanism to identify the cable and the medical components to the computer. Optionally, the invention may comprise a bespoke connector e.g. to prevent connection of foreign cables.

Optionally, in particular embodiments, the medical data gathering module may monitor and detect any one or more or any combination of the following physiological conditions: electrocardiogram (ECG) signals; invasive or non-invasive blood pressure; spirometry (lung function); and pulse oximetry; temperature; both invasive and non-invasive blood pressure monitoring; audiometry testing; retinal testing; ultrasound screening; dermatology screening (image capture); imaging, tissue viability and wound care screening; video endoscopy; video for remote consultations; video conferencing; audio for detection of heart and/or lung sounds; scaliometer (height); foetal heart Doppler ultrasound audio acquisition and analysis and weighing scales.

Electrical components of the cable and/or computer in one example embodiment may contain improved circuitry that may be capable of measuring and/or detecting ECG signals. In certain embodiments, the improved circuitry provides a method of data transfer to reduce or substantially avoid data loss within the bandwidth required by a standard PC.

Alternatively or in addition the improved circuitry may provide a safe method of connecting a patient directly to a computer system and network, for example by means of defibrillation protection circuits in the cable and/or within the computer e.g. optical isolator circuit(s) on the medical data gathering circuit board. For example, the improved circuitry may comprise a first stage where an input to the ECG consists of a defibrillator and/or mains potential electric protection. This protection may be contained within the cable and/or may also be within the first stage of an ECG input.

Optionally, a physiological signal sensed from the skin of a patient by one or all electrodes of the cable may form an input to a buffer amplifier. Outputs of the buffer amplifier may be connected to a resistor array network in, for example, a star delta formation. A centre of the resistor network may form a common signal which may be used for common mode signal rejection and may form an input to a separate amplifier which is connected and drives the screen of the cable. The aim of this is to reduce noise which is common to all electrodes and reduce capacitively generated noise in the cable. Optionally, each electrode or considered lead position may have its own buffer amplifier and the output of the buffer amplifier may be routed to the input of a different amplifier. The different amplifier circuit may provide a signal gain of approximately 140 and may provide a high degree of slew rate limiting. Quad amplifiers may be used where the first stage of the quad amplifier serves as a fixed gain. The second stage may serve as a slew rate limiter. The output of third and fourth stages may be common together and may be used as comparators to detect if the electrode has become removed from the patient's skin, resulting in amplifier saturation. The output of the second stage of the quad amplifier and the common output of the third and fourth stages may form independent inputs to a plurality of analogue to digital converters.

In one example embodiment, the invention may therefore be computationally efficient by providing a plurality of analogue to digital converters in the improved circuitry. Optionally in addition, in a further effort to reduce computational cycles, the controlling signals to the analogue to digital converters may be common and the analogue to digital converters may be set to run in synchrony. For example, at least two, and in particular three analogue to digital converters may be utilised thus reducing the computational cycles to address the analogue to digital converters three fold. The analogue to digital converters may be arranged to sample the signals at a rate of 1 kHz to 20 kHz, or more, say once every 0.5 ms (millisecond), or once every 1 ms. Each output from the plurality of analogue to digital converter may be interfaced to high speed electromagnetic isolators with a high degree of isolation from the input to the output to ensure patient safety.

Optionally, an integrated circuit, such as a fully programmable gate array (FPGA), optionally having a first in first out (FIFO) memory module may be employed to sample from the isolators (and hence from the analogue to digital converters) optionally, at a pre-programmed rate of, for example, between about 1-10 kHz, say at 1 kHz or once every millisecond. Optionally, this may be half the rate of the sampling by the analogue to digital converters. This reduces computational cycles and in particular the computational burden on the computer because this part of the circuit is independent from the host computer. The computer may then sample the first in first out buffer at a sample retrieval request rate of between, for example, about 1-20 Hz to empty the buffer and store the data into the computer memory. The actual rate of transfer of sampled data may be within the sample rates achievable by data bus architecture embedded within central processing units (typically much faster than 10 kHz). The data may then be ready for analysis by suitable software and displayed on a display of the computer or transmitted. For example, the data may first be compressed and then encrypted to preserve patient confidentially before being stored into memory of the computer and/or transmitted to a remote location via a network connection. Once received at the remote location, the data may be de-encrypted and decompressed in order to be displayed on another computer.

This electrocardiogram circuitry and signal analyser may be housed in a computer or within a laptop computer such as on a shelf which may, for example fit into a standard computer ROM bay drive. Any personal computer with available bays or suitable laptop computer may be used for the present invention but in one example embodiment, optionally, it is preferred if the computer is fitted with a revision controlled mother-board. Optionally, it is also preferred that the computer is fitted with a medical grade power supply. The computer used in the present invention may be any suitable computer. The computer may comprise a recess within which, for example, a ROM enclosure may be inserted. A circuit board may also be attached to, for example, a shelf in the computer. A front face plate may also be attached to the front of the computer. The front face plate may comprise an aperture through which the computer may be connected to medical apparatus. The computer may comprise an electronic circuit which is designed to specifically use less computational cycles and therefore be computationally efficient in sampling physiological signals. For example, the electrocardiogram may comply with EN ISO 60601-2-25 relating to ECG equipment and ENISO 60601-2-27 relating to ECG monitoring equipment.

According to a further aspect of the present invention there is provided a method of detecting and transmitting information relating to the physiological condition of the patient to the computer using apparatus comprising cable and a computer according to one aspect of the invention.

According to a further aspect of the present invention there is provided apparatus for detecting and/or monitoring a physiological condition of a patient, said apparatus comprising: a computer; and a cable comprising at least one lead capable of connecting the cable to a computer and at least one further lead comprising medical apparatus capable of detecting a physiological condition of a patient.

The computer used may be a desktop computer or alternatively may be a laptop computer. The computer may be specially adapted for the present invention. For example, the computer may comprise an amplifier such as an ECG amplifier. Optionally, the computer may comprise an increased depth to accommodate an ECG interface and/or a blood pressure interface. Optionally, the computer may also be portable such as a laptop computer. Within the computer there may be monitoring apparatus for monitoring a patient's vital signs. The apparatus according to the present invention may allow a healthcare worker to make a decision on the vital signs health status of a patient without the need for any other external patient monitoring equipment required. The electronic circuitry of the data handling module overcomes the technical difficulties relating to computer processing power and real time analysis when using, for example, the relatively low clock speed of the operating system by providing a separate medical data handling facility. In more detail:—

1. Diagnostic quality patient monitoring requires a sample rate of the signal that is reliable with no data loss i.e. (1 to 10 kHz)×24 signals to sample.

2. Although computers are fast (currently around 3 GHz), the operating system clock actually runs quite slowly (around 20 Hz).

3. The present inventors had to find a way of monitoring the patient with diagnostic quality under the constraints of the operating system.

4. Optionally, the circuitry samples all 24 of the analogue signals at 1 kHz (e.g. all 24 channels at every 1 ms) or at 2 KHz (e.g. 24 channels once every 0.5 ms).

5. Optionally, A/D's operate in synchrony to sample the data to save computation cycles 6. Optionally, the data is held in a medical data handling module, optionally comprising for example a FIFO buffer, optionally, in 0.25 ms, 0.5 ms, 1 ms, 2 ms, 5 ms, 10 ms, 20 ms, 25 ms, 30 ms, 50 ms chunks. Optionally, the FIFO buffer may be 4 kbits or 32 kbits. For example, if 54 bits of data are held in 1 ms groups of data than the 4 kbit FIFO can hold 54 bits×74 ms=3996 bits of data i.e. 74 groups of data of size 54 bits. A 32 kbit FIFO would be able to hold 592 ms of data held in 54 bit groups of data (54 bits×592 ms=31968 bits) i.e. 592 bits of data of size 54 bits.

7. Optionally, the software then samples the data and is transferred to the PC CPU at a leisurely 20 Hz.

Thus the present inventors have found a way to transfer the data with minimal data loss.

In a particular embodiment of the present invention, a user may affix ECG electrodes to a patient's chest in the normal way, but plug the electrode cables directly into the computer via a built in ECG socket. The ECG socket may be wired to circuitry which amplifies and signal conditions the ECG waveform. The signal may be digitised before being electrically isolated. A digital signal emitted from the apparatus may be routed to an internal bus of the computer, directly to the CPU for analysis. The computer may perform cardiac analysis and may display waveforms and results on a screen. The screen may be a standard LCD screen. The user may also wrap a blood pressure cuff around a patient's arm and plug a pneumatic hose directly into a blood pressure port on the side of a computer. The computer may then perform blood pressure analysis and display waveforms on a display screen. The circuitry required to perform the detection and analysis of a patient's vital signs may be built into and incorporated into a computer such as a laptop computer. Typically, the circuitry which interfaces with the computer for either or both, for example, ECG and blood pressure analysis, may utilise an improved method of data transfer which uses very low computer processing power. The computer may also comprise means such as memory and associated software which may save all results for future pending analysis or comparison of future recordings. The computer may also be configured to send encrypted vital signs data through an available network connection to a specialist unit (accident and emergency or coronary care unit) which may help make an informed decision on the health status of a patient. Data sent across a network may also be automatically encrypted by the device to prevent patient data information being accessed by an unauthorised person. The laptop computer may also be suitable for transmitting data for "live" remote monitoring by a special unit. A web cam may also be installed into the computer to enable a remote specialist to see the patient via video or captured pictures which will help with remote diagnosis, for example, skin cancer, wound, fracture advice and the like. Alternatively or in addition, the apparatus may comprise video conferencing capability e.g. for real time video conferencing with a health care professional. This may be in addition to the functionality of video or image recording of a physiological condition. Computer software in the computer may also be used to access local patient information databases to update the patient record with the current results and any findings or further information or referral advice. The apparatus according to the present invention may therefore be used to make more acute or emergency decisions. For example, currently if a person has suffered a myocardial infarction (i.e. a heart attack), there is a time period in which a patient needs to have specialist treatment. This time period is often critical especially if a patient is away from specialist help. The apparatus according to the present invention may be used to help local healthcare personnel to administer specialist treatment under the remote specialist advice. The apparatus according to the prevent invention may therefore help to prevent unnecessary journeys to hospital. Currently remote or rural patients have to travel considerable distances to gain specialist advice or treatments, when actually, some patients do not need to make such a journey. The apparatus according to the present invention may therefore help a local healthcare professional make an informed decision on transferring a patient to a territory hospital or specialist unit.

The apparatus therefore provides advantages over existing methods relating to patient safety (where devices may be plugged into an unknown computer which may not be approved for safe use within the patient environment) and convenience (because all of the required functions are within 1 unit).

A method of assessing the ECG of a subject under test may comprise any one of or combination of the following steps: performing an ECG test at recording apparatus located at a first physical location; propagating from the first physical location via a network connection, to a receiver apparatus located at a second physical location, spaced from the first location; conducting at a receiver computer the assessment of the ECG and generating a test result; and propagating from the receiver computer to the recording apparatus a clinical assessment statement; and presenting the result in a readable manner to a user at the recording apparatus. The method may also comprise the step of propagating from the recording apparatus at the first physical location via a network connection which also includes the step of propagating from the recording apparatus via a wireless network connection. The ECG signal may be encrypted for the process of transmission, and encryption reversal at the receiver apparatus.

The patient recording may be capable of displaying the clinical data in predetermined format, displaying the electrocardiograph data in a graphical format, using software custom design for this purpose. The patient report may include addition fields for use by the user, wherein the user is capable of adding to the patient report within the addition fields. The additional fields may be capable of receiving text information from a user who is a cardiologist and wherein the text information includes analysis and diagnosis data.

Optionally, it is preferred that the apparatus may be able to filter noise. Optionally, noise filtering can be done in software and/or in the electronics. Optionally raw data is delivered to the software in the microprocessor with minimal or no filtering. Optionally, filtering is done in the software using a finite impulse response (FIR) filter or using an infinite impulse response (IIR) filter. Optionally, the apparatus may signal condition the signal by buffering the shape of the signal to the A/D converter(s) on the way to the FPGA. Optionally, there is also provided a means of the signal sensed from each electrode being routed to a buffer amplifier and each electrode has its own buffer amplifier. Typically, the apparatus may utilize a plurality of analogue to digital converters arranged in such a way as to enable simultaneous or substantially simultaneous monitoring of each electrode to reduce computation operations and therefore be computationally efficient.

Optionally, the invention seeks to ensure that a multi channel ECG may be simultaneously monitored, for example by using at least two analogue to digital converters, whilst using the minimum of computing effort through use of minimal computing operations and may safely be used to perform medical measurements.

BRIEF DESCRIPTION OF THE DRAWINGS

Example embodiments of the invention will now be described by way of example only with reference to the following figures in which like reference numerals refer to like referenced features.

FIG. 1 shows a schematic perspective view of a personal computer and its housing and an exploded perspective view of an ECG interface card assembly according to an example embodiment of the invention.

FIG. 2 shows an exploded perspective view of an ECG interface card assembly according to an example embodiment of the invention.

FIG. 3 shows an exploded perspective view of a blood pressure (BP) interface card assembly according to an example embodiment of the invention.

Figure 23:
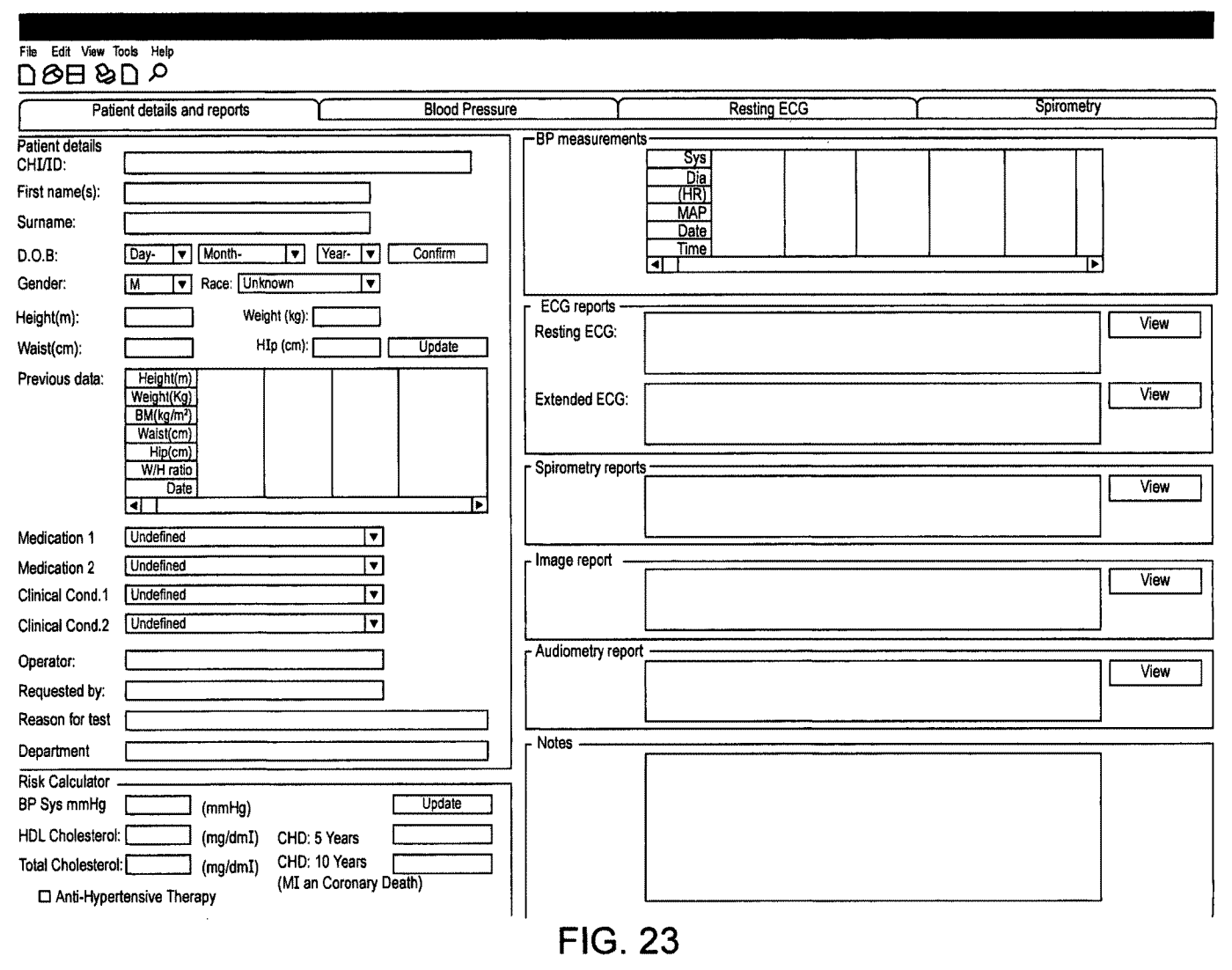

FIG. 23 shows a representation of a user interface screen for patient details and reports according to an example embodiment of the invention.

Figure 27:
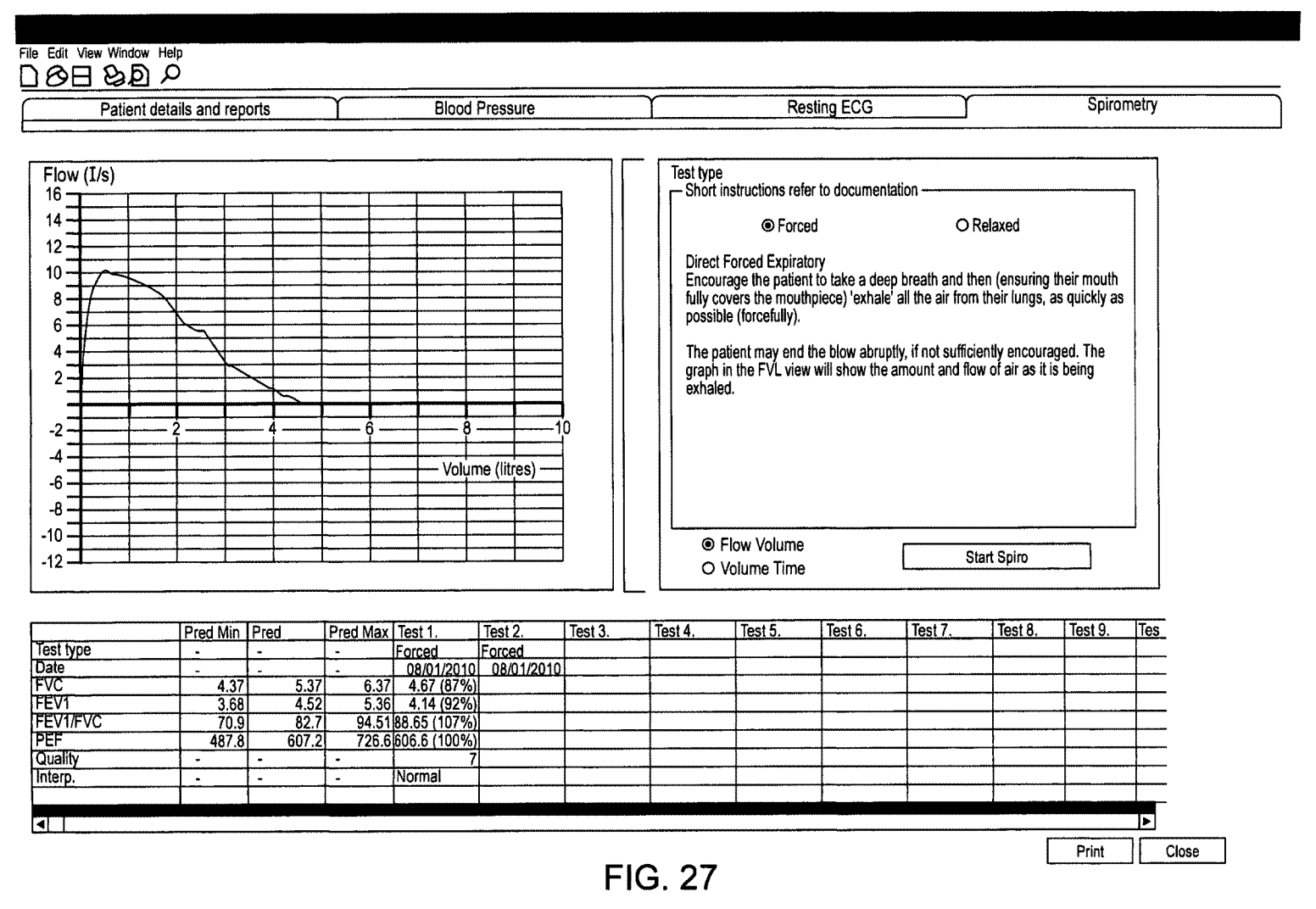

FIG. 27 shows a representation of the user interface screen for use with a spirometer according to an example embodiment of the invention.

FIG. 28 shows a table of N data bits relating to ECG data, skin temperature data and BP data according to an example embodiment of the invention.

DETAILED DESCRIPTION OF THE DRAWINGS

Figure 4:
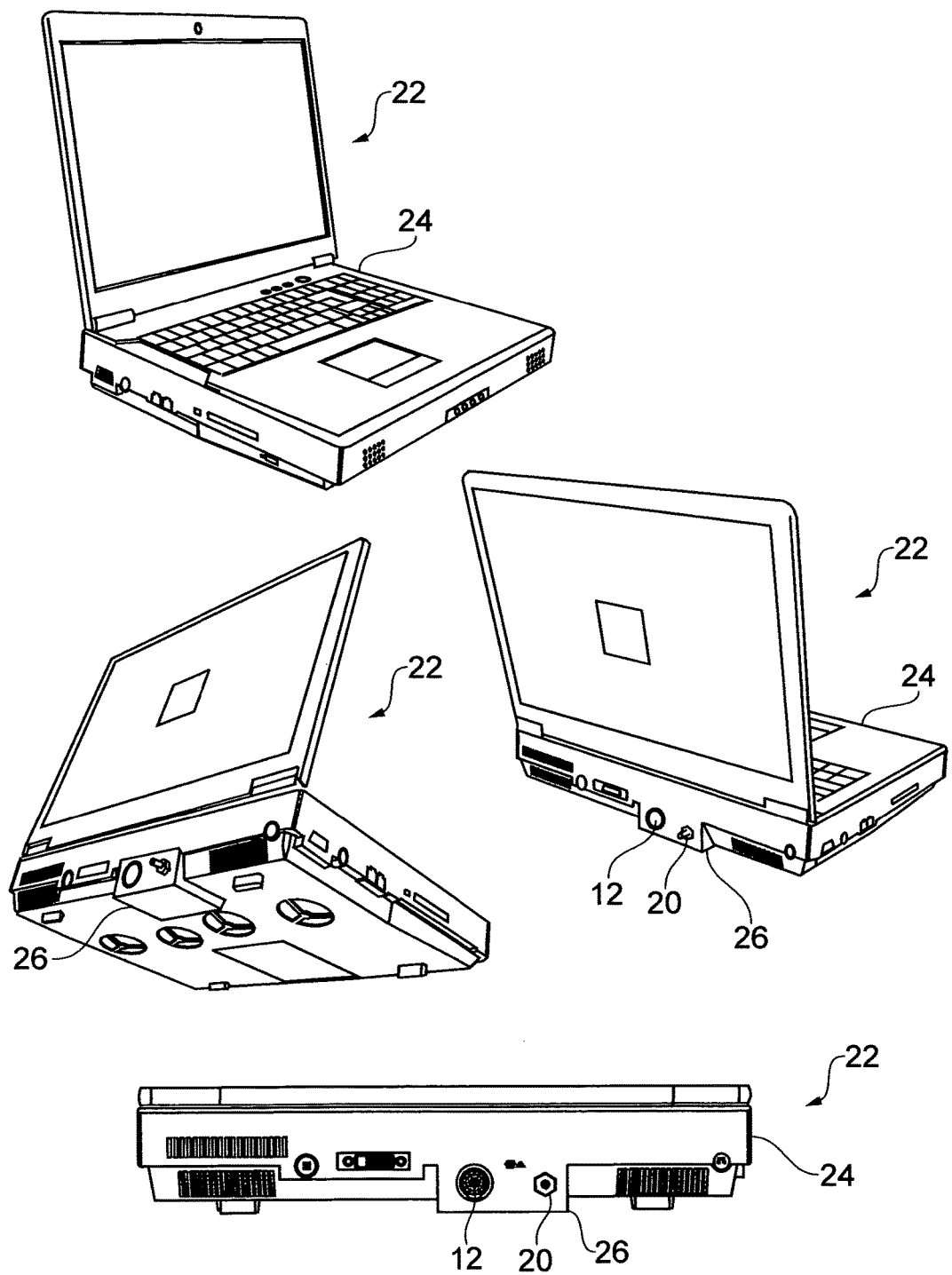
FIG. 4 shows four perspective views of a laptop computer and its housing according to an example embodiment of the invention.

Turning now to the figures, FIG. 1 shows apparatus 1, according to one example embodiment of the invention.

Apparatus 1 comprises a personal computer (PC) 2 having housing 4 and a medical data gathering module 6. Here, medical data gathering module is in the form of an electrocardiogram (ECG) interface assembly 6 mounted in a PC ROM bay 10 so that a front wall 7 of ECG interface assembly 6 forms part of housing 4 of the PC 2 (see FIG. 2). In FIG. 2, an ECG socket 12 is mounted in a front wall or front face plate 7 for providing direct connection to a patient via an ECG patient cable (not shown). An ECG interface card 14 is provided within ECG interface assembly 6 to mount ECG power, control and data gathering components thereon.

In FIG. 3, an additional or alternative medical data gathering module is provided in the form of a blood pressure (BP) interface assembly 16. In this example, BP interface assembly 16 is for non-invasive blood pressure measurement and has a lid 8. A BP interface card 18 is provided within BP interface assembly 16 to mount BP power, control and data gathering components thereon as well as a pump 21. Alternatively, pump 21 is located adjacent BP interface card 18. The pump 21 leads to a cuff connector 20 via a pump connector 20'. BP interface assembly 16 is mounted in a PC ROM bay 10 (see FIG. 1), so that a front wall 7 (see FIG. 2) of BP interface assembly 16 forms part of housing 4 of the PC 2. The BP cuff connector 20 is mounted in the front wall 7 of BP interface assembly 16 for providing direct connection to a patient via a BP (air) cable and cuff (not shown).

FIG. 4 shows perspective views of a laptop computer 22 adapted to form apparatus according to one example embodiment of the invention. The laptop computer 22 has a housing 24 and, in this example embodiment, a housing extension 26. As in the case of a desktop computer 2 seen in FIG. 1, one or more data gathering modules, for example, in the form of ECG interface 6 and/or BP Interface assembly 16 are built into the laptop computer and are not visible here being hidden by housing 24. However, an ECG socket 12 and a BP cuff connector 20 for providing direct connection to a patient are visible in housing 24. In this example, these are located in optional housing extension 26. The housing extension 26 has been formed in line with and contiguous with the rear wall of housing 24 of laptop computer 22, so as to provide a clean finished line to rear wall of housing 24.

Figure 29:
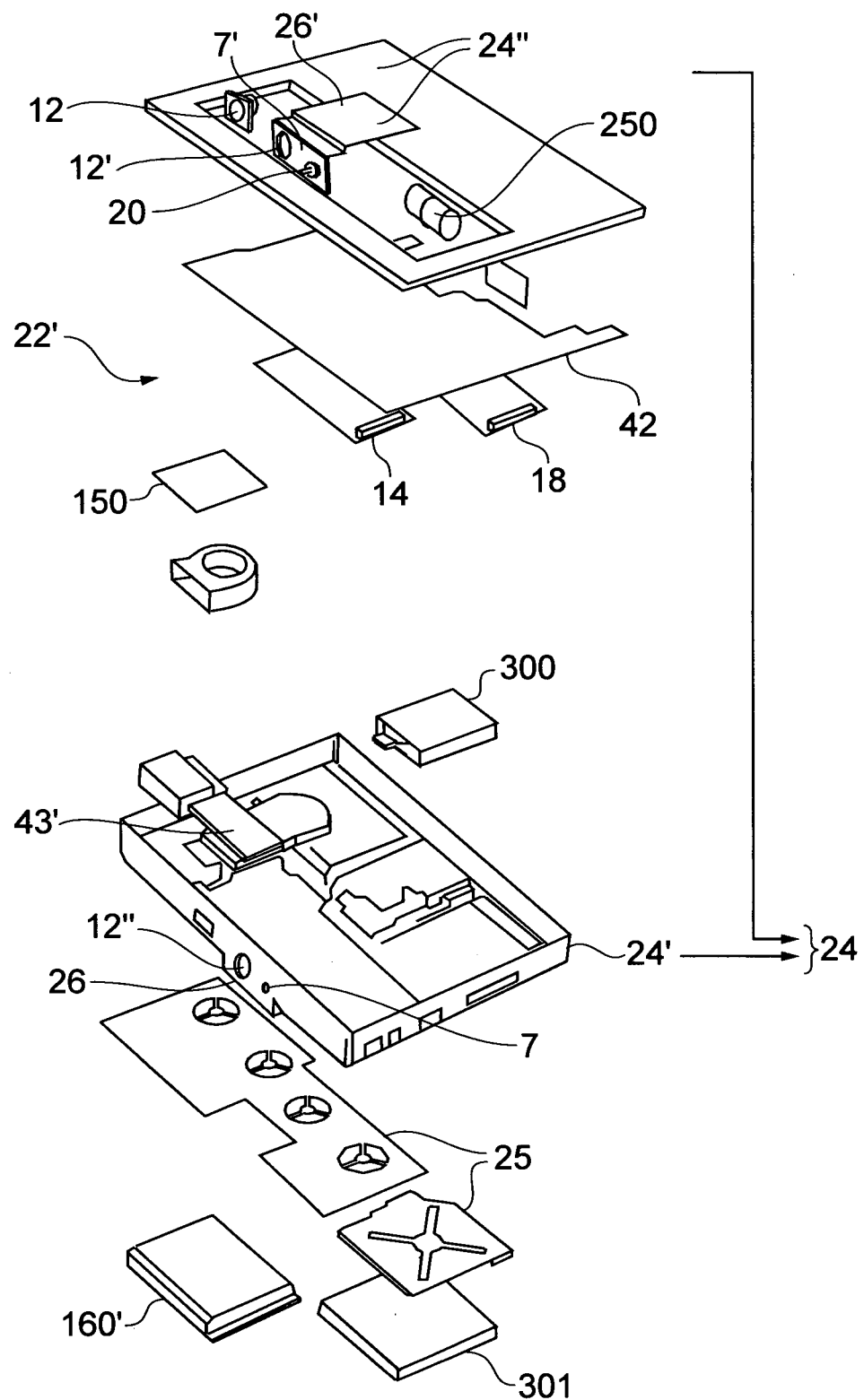
FIG. 29 shows an exploded view of part of a laptop computer according to an example embodiment of the invention.

Briefly turning now to FIG. 29, an exploded view of part of a laptop computer base 22' is shown. Optionally, laptop computer base 22' has a display (not shown). Laptop computer 22' has a housing assembly 24 comprising a housing base 24' and a first part of a housing lid 24". A further cover (not shown), optionally, in the form of a keyboard, may be fixedly mounted on housing lid 24" to form a lid of unitary housing 24. Covers 25 below base 24' may also form a part of unitary housing 24, for example when fixedly mounted on housing base 24'. Housing lid part 24" is typically formed from a metal plate for strength and optionally has an extension 26' having a front plate 7' with an aperture 12' and another aperture for mounting a cuff connector 20. A pump 250 for connecting to cuff connector 20 is shown. ECG socket 12 is shown, and in normal use, is fixedly mounted in aperture 12'.

Laptop 22' comprises a revision controlled mother board 42 to which ECG interface card 14, BP interface card 18, FPGA board 150 and CPU assembly 43' are connected and/or mounted thereon. Laptop 22' also comprises a hard drive 300, rechargeable battery 160' and DVD drive 301. A front wall 7 of housing extension 26 in housing base 24' is arranged so that aperture 12" is aligned with aperture 12' for mounting ECG socket 12 therein. Likewise an aperture in front wall 7 is provided for aligning with cuff connector 20.

Thus, in FIGS. 1, 4 and 29, the PC 2 and laptop computer 22/22' also typically comprise at least one core microprocessor and standard operating system such as Microsoft Windows®, Apple Mac® or Linux operating system. Thus, apparatus according to the invention provides all the normal functionality of a personal computer or laptop computer, as well as one or more medical data gathering modules. In these embodiments, this is provided within a single housing (housing 4 in FIG. 1 and housing 24 in FIG. 4). By providing both data gathering and computing functionality within a single unitary integrated housing, a number of advantages are provided. Firstly, whilst taking measurements with a patient, a HCP has access to all the usual computing functionality for carrying out other parallel activities (e.g. Microsoft Word®, Microsoft Outlook® for email etc). Secondly, the data collected by the one or more data gathering modules is immediately available for use by the usual suite of programs available on computers, e.g. word processing, spreadsheets, email etc). Thirdly, there is no need to provide a separate computing facility separate from the medical apparatus, since this is provided along with the computer. By utilizing the features of the invention and in particular the features of claim 1 of the invention, the medical device side of the apparatus can operate with minimal affect on the operation of the computer and vice versa, i.e. the computer can operate with minimal effect on the operation and indeed data collection of the medical device. Fourthly, because the computer either desktop or Laptop is adapted, in effect now a piece of medical apparatus and easily identifiable as such (for example in one embodiment by the presence of one or more sockets or connectors (12, 20) and/or housing extension 26 in the housing 4, 24), it is a much less attractive proposition for theft, an important criterion when expensive computing devices, especially portable ones, are used in a public health care setting.

In an alternative embodiment (not shown), a medical data gathering module such as ECG interface assembly 6 and/or BP interface assembly 16 can be mounted in a separate second housing, distinct and separate to a first housing 4 or 24. In such circumstances, wired or wireless communication components may be built into each housing to enable communication between the first and second housings, and the components therein. In one version of this alternative embodiment, medical data handling means for sampling data from medical data gathering modules (e.g. from modules 6 and 16) is built into the first (computer) housing 4, 24. In another version of this alternative embodiments, medical data handling means for sampling data from the medical data gathering modules e.g. from 6, 16, is built into the second housing (not shown) along with the medical data gathering modules. In either case, where two housings are provided, it may be advantageous e.g. from a space saving perspective, if one housing is adapted so the other can be located above it, for example, by having a flat upper surface, or other suitable mounting means. Alternatively or in addition, the size and shape of an outer periphery of the one housing may be substantially similar or identical to that of the other housing. For example, the size and shape of the second housing may be substantially similar or identical to that of the first housing so that the first PC/laptop housing 4, 24 can be placed thereon and adopt a similar overall outline. This arrangement is particularly suitable for a laptop computer embodiment such as that shown in FIG. 4, so that first laptop housing 24 may be placed upon the second housing containing the medical data gathering modules. Alternatively, and particularly suitable for a desk top PC housing 4 (see FIG. 1), the upper surface of the PC housing may be adapted so that the second housing can sit thereon. For example, it may be that the size and/or shape of an upper portion of the first (PC) housing may be substantially similar to or identical to that of the second housing containing the medical data gathering modules so that the second housing can be placed thereupon (not shown).

Figure 5:
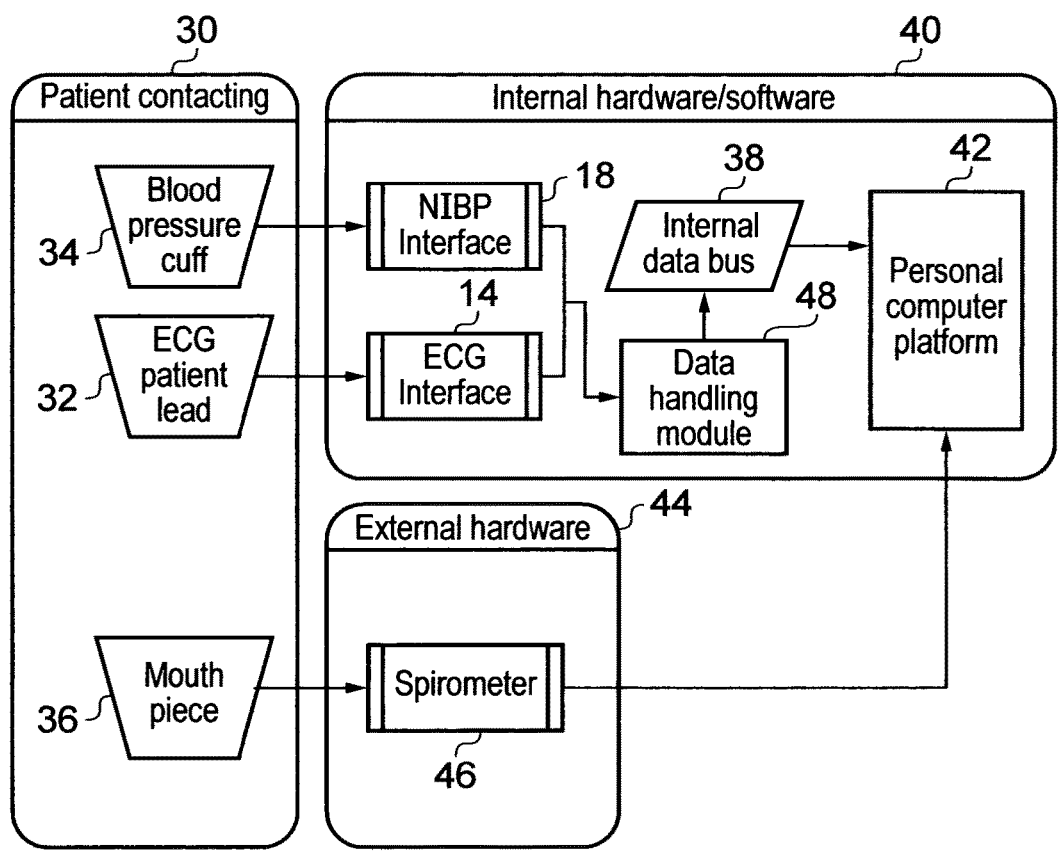
FIG. 5 shows a schematic functional block diagram of apparatus according to an example embodiment of the invention.

FIG. 5 shows schematic functional block diagram of apparatus according to one embodiment of the invention. FIG. 5 shows patient contacting hardware 30 comprising an ECG patient lead 32, a blood pressure cuff 34 and a spirometer mouthpiece 36. FIG. 5 also shows internal hardware and software 40 comprising an ECG interface card 14, a BP interface card 18, an internal data bus 38, a personal computer platform 42 comprising a microprocessor (such as a PC motherboard) and a separate data handling module 48. Additional internal hardware in the form of a spirometer 46 is shown connected directly to the PC platform 42. BP cuff 34 connects to PC platform 42 via, firstly, BP Interface card 18 and, secondly, via data handling module 48. Similarly, ECG patient lead 32 connects to PC platform 42, firstly, via ECG interface 14 and, secondly, via data handling module 48.

Figure 6:
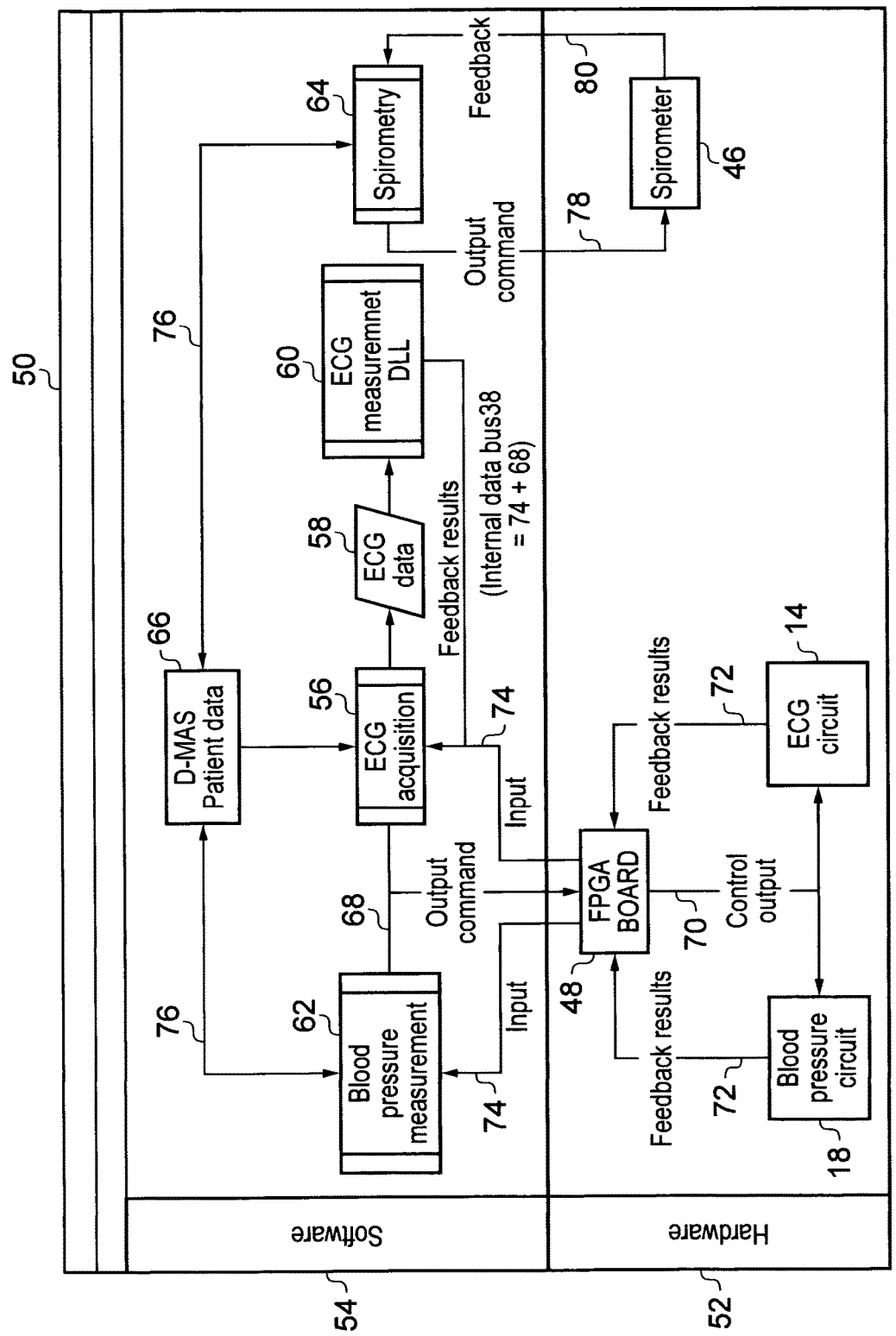
FIG. 6 shows a schematic block diagram of functional and software modules of apparatus according to an example embodiment of the invention.
Figure 7:
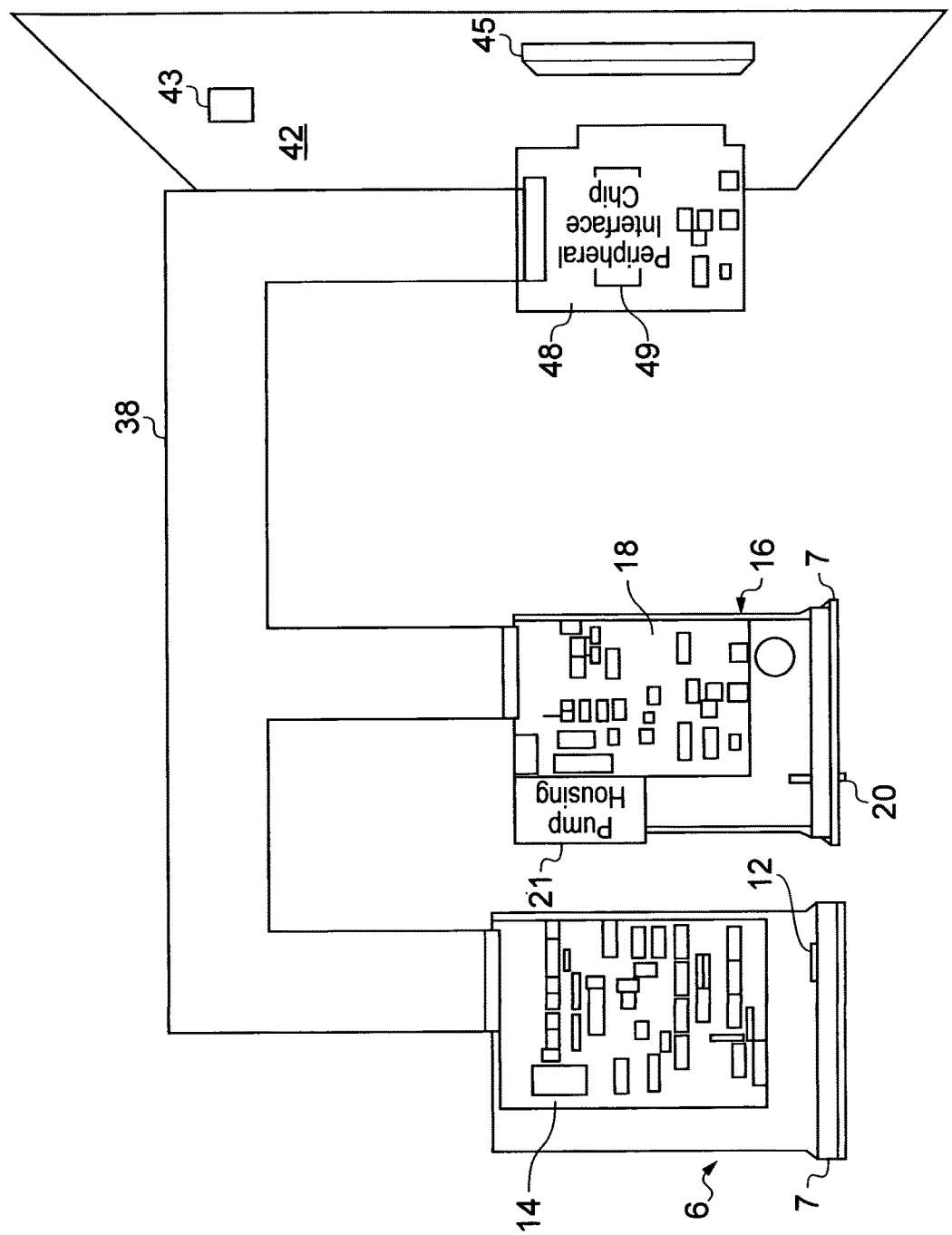
FIG. 7 shows schematic diagram of ECG and BP interface cards, data handling module interface card and computer microprocessor motherboard according to an example embodiment of the invention.

FIG. 6 shows a schematic block diagram of the hardware and software functional modules of apparatus according to one embodiment of the invention. Here the apparatus comprises an analysis system 50 having hardware modules 52 and software modules 54. ECG interface card 14 and BP interface card 18 are connected to an ECG acquisition module 56 and BP measurement module 62 via ECG and BP output command lines 68, control lines 70, ECG and BP data feedback lines 72 and ECG and BP data input lines 74 via medical data handling module 48. In practice output command lines 68 and input data lines 74 are part of internal data bus 38 (see FIG. 5). Thus lines 68 and 70 transmit control signals and lines 72 and 74 feedback data sampled as described elsewhere herein. Similarly, spirometer 46 is controlled by and feedbacks to spirometry measurement modules 64 via output command line 78 and data feedback line 80. Patient data is fed into a patient data software module 66 (and optional patient data file) by bidirectional patient data input line 76. The patient data may be encrypted and/or compressed within a special format file. ECG acquisition module 56 connects to an ECG data module 58 which in turn connects to an ECG measurement and calculation module 60 (here a dynamic link library module). Optionally, ECG feedback line 74 also feedbacks results to ECG measurement and calculation module 60 from medical data handling module 48 (optionally in the form of an FPGA module). FIG. 7 shows an ECG interface assembly 6, ECG interface card 14 and ECG socket 12 mounted in front wall 7. FIG. 7 also shows BP interface assembly 16, BP Interface card 18, pump 21 and cuff connector 20 mounted in front wall 7. An interface data bus 38, here a 40 way IDE (integrated drive electronics) connector links ECG interface card 14 and BP Interface card 18 to medical data handling module 48, for example, here a peripheral interface board or a field programmable gate array (FPGA) board. A medical data handling microprocessor 49 is mounted on medical data handling module 48. Medical data handling microprocessor 49 may be a system-programmable-on-a-chip (SPOC) in the form of a field programmable gate array (e.g. an FPGA manufactured by Altera) as will be described in more detail later. Alternatively, an ASIC such as a Rapid Chip from LSI may be used as medical data handling module. The PC motherboard 42 having computer microprocessor 43 and PCI standard card socket 45 is also shown. It should be noted that medical data handling microprocessor 49 is separate and distinct from computer microprocessor 43. In this example embodiment, medical data handling module 48 is also provided on a PCI standard card having a PCI standard connections for slotting into PCI standard card socket 45 on PC motherboard 42. Typically, this is used in the desktop PC version. In the laptop computer version, the data handling module 48 typically communicates with the mother board 42 via a USB wire connection located internal to the laptop housing 24 (see FIGS. 4 and 29), or via wireless connections where a first and second housing are provided. Other variations on these arrangements can be envisaged by those skilled in the art. It will be also understood by those skilled in the art that whereas both ECG and BP data gathering modules are described, one or both or alternate medical data gathering modules may be used.

Figures 8, 9:
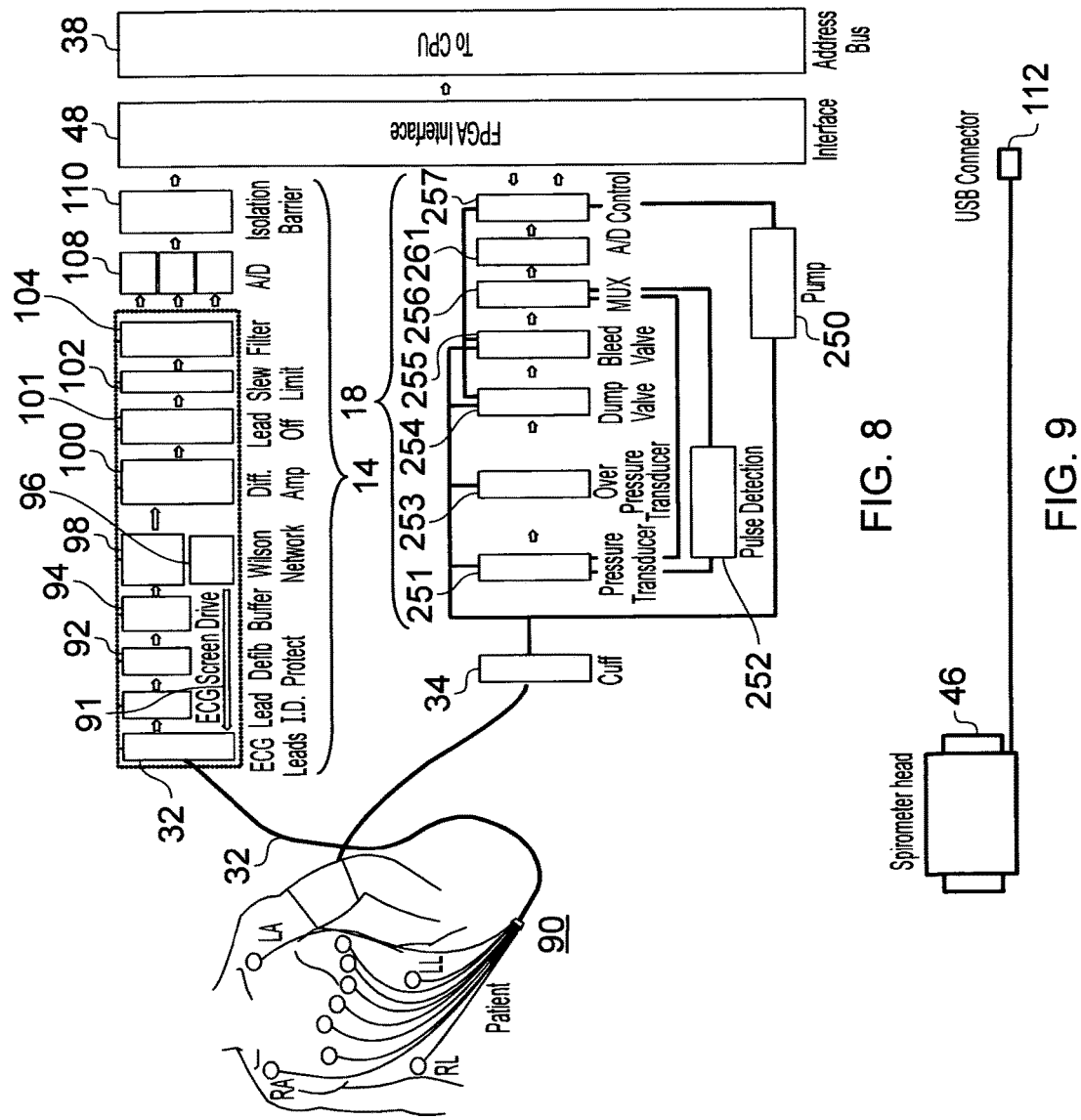
FIG. 8 shows schematic block diagram of various components for ECG and BP measurements, and interconnections via data handling module interface card and internal computer address bus according to an example embodiment of the invention.
FIG. 9 shows a schematic diagram of a further medical data gathering module in the form of spirometer head and a universal serial bus (USB) connector according to an example embodiment of the invention.

FIG. 8 shows ECG and BP measurement components in more detail. A patient 90 is connected to ECG interface card 14 via an ECG patient lead 32. ECG interface card 14 comprises a first protection circuit, for example, in the form of defibrillation protection circuit 92, lead identifier circuit 186, a buffer circuit 94, ECG screen drive amplifier 96, a Wilson network circuit 98, a differential amplifier circuit 100, a lead off circuit 101, a slew rate limiter circuit 102, a filter circuit 104, at least one and here three analogue to digital converters 108 and a second protection circuit, for example, in the form of an isolation barrier 110. ECG interface card 14 connects to data handling module 48 in the form of a bespoke interface card that connects via internal data bus 38 to computer microprocessor 43 (not shown). An ECG lead screen drive signal 91 for screening the ECG leads 32 is derived from the Wilson network 96. A medical data handling module 48, here in the form of an FPGA module, and an internal data bus 38 are also shown.

BP interface card 18 comprises pressure transducer 251, pulse detection circuit 252, over pressure transducer 253, dump valve 254, bleed valve 255, multiplexer 256, analogue to digital (A/D) converter 261, pump control circuit 257 and pump 250. A cuff 34 connects the BP interface to a patient.

FIG. 9 shows a spirometer head 46 connected to a USB connector 112 for connecting to a USB port in the housing 4, 24 of PC 2 or laptop 22. Thus as shown in FIGS. 8 and 9, two medical data gathering modules 14, 18 are connected via medical data handling module 48 to internal communications bus 38. A separate medical data gathering module, here a spirometer head 46, is connected via USB connector 112 to internal communications bus 38 and directly to microprocessor 43 (seen in FIG. 7). One or more additional medical data handling modules, such as any medical data gathering module described herein, may thus be added and connected to the microprocessor e.g. using USB connectors to connect to internal data bus of the microprocessor. It is therefore possible to add additional functionality with only additional software changes required, no or minimal hardware changes required. Thus in one example embodiment, the present invention provides seamless addition of separate functionality of any one or more medical data gathering modules by plugging directly into internal communications bus 38, e.g. via USB ports or other plug and play facility by appropriate modification and/or upgrade of functionality of internal software of the apparatus.

Figure 10:
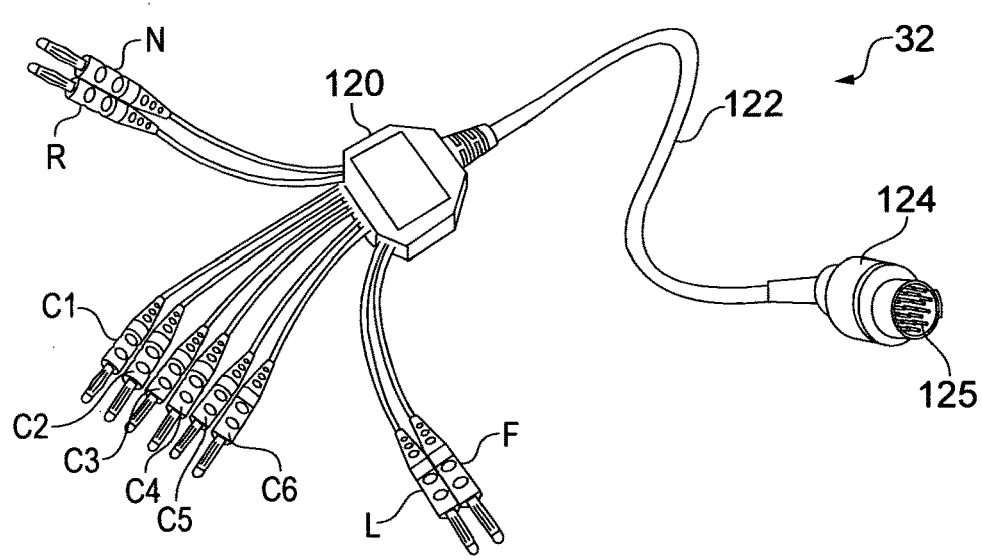
FIG. 10 shows, schematic perspective view of an example ECG cable according to an example embodiment of the invention.
Figure 11:
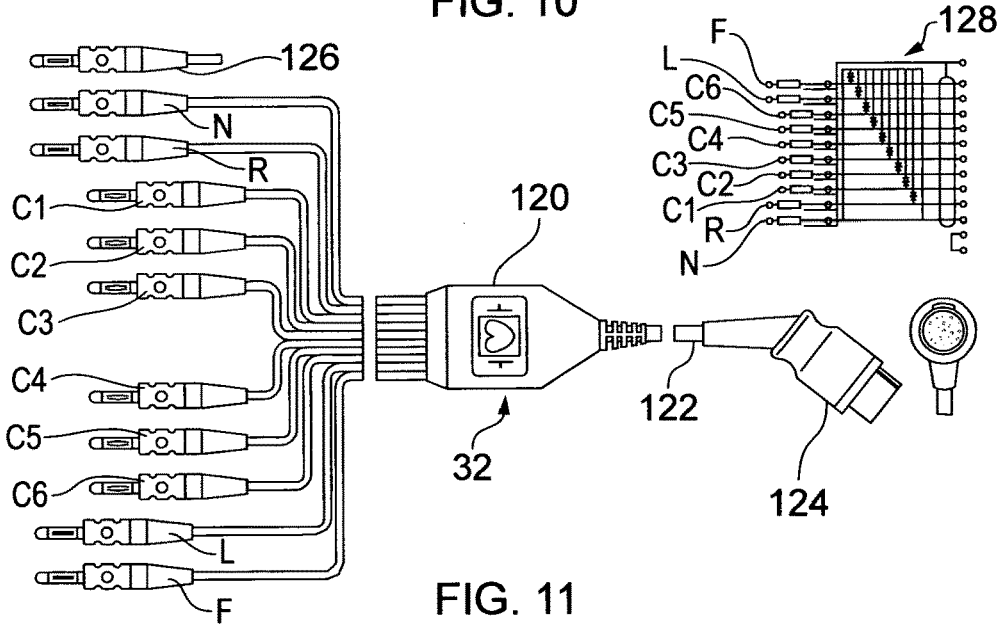
FIG. 11 shows a plan view of an example 10 lead ECG cable according to an example embodiment of the invention.

FIGS. 10 and 11 show respectively, perspective and plan views of a ten lead ECG patient cable 32. Ten lead ECG cable 32 has an optional central connection point in the form of an ECG lead hub 120, ECG connecting lead 122, and ECG cable plug 124. ECG lead plug 124 has numerous pins 125 connected to patient lead connections N, R, C1, C2, C3, C4, C5, C6, L and F (or RA, LA, LL, C1, C2, C3, C4, C5, C6, RL and S depending upon terminology used) via ECG lead hub 120. Lead connections, N, R, C1, C2, C3, C4, C5, C6, L and F connect to the body of a patient in a standard pattern well documented and understood by those skilled in the art. In brief, six leads namely C1, C2, C3, C4, C5 and C6 are placed around the chest using connection leads and electrode patches for detecting heart rhythm signals with respect to a lead placed on a limb. This gives six waveforms. Three original lead positions (as in a 3-ECG cable) gives three more signals, then with respect to a second (other limb lead) this gives three new augmented waveforms. In total 12 waveforms result from a ten lead ECG measurement.

Figure 12:
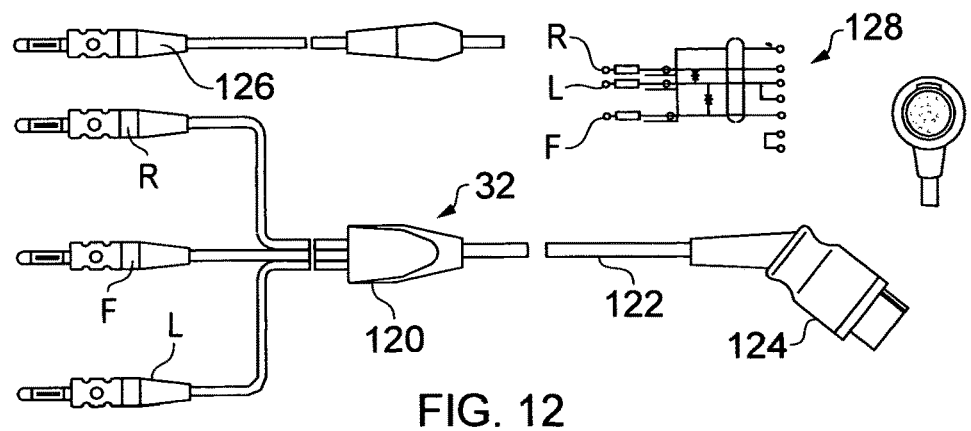
FIG. 12 shows a plan view of an example 3 lead ECG cable according to an example embodiment of the invention.
Figure 13:
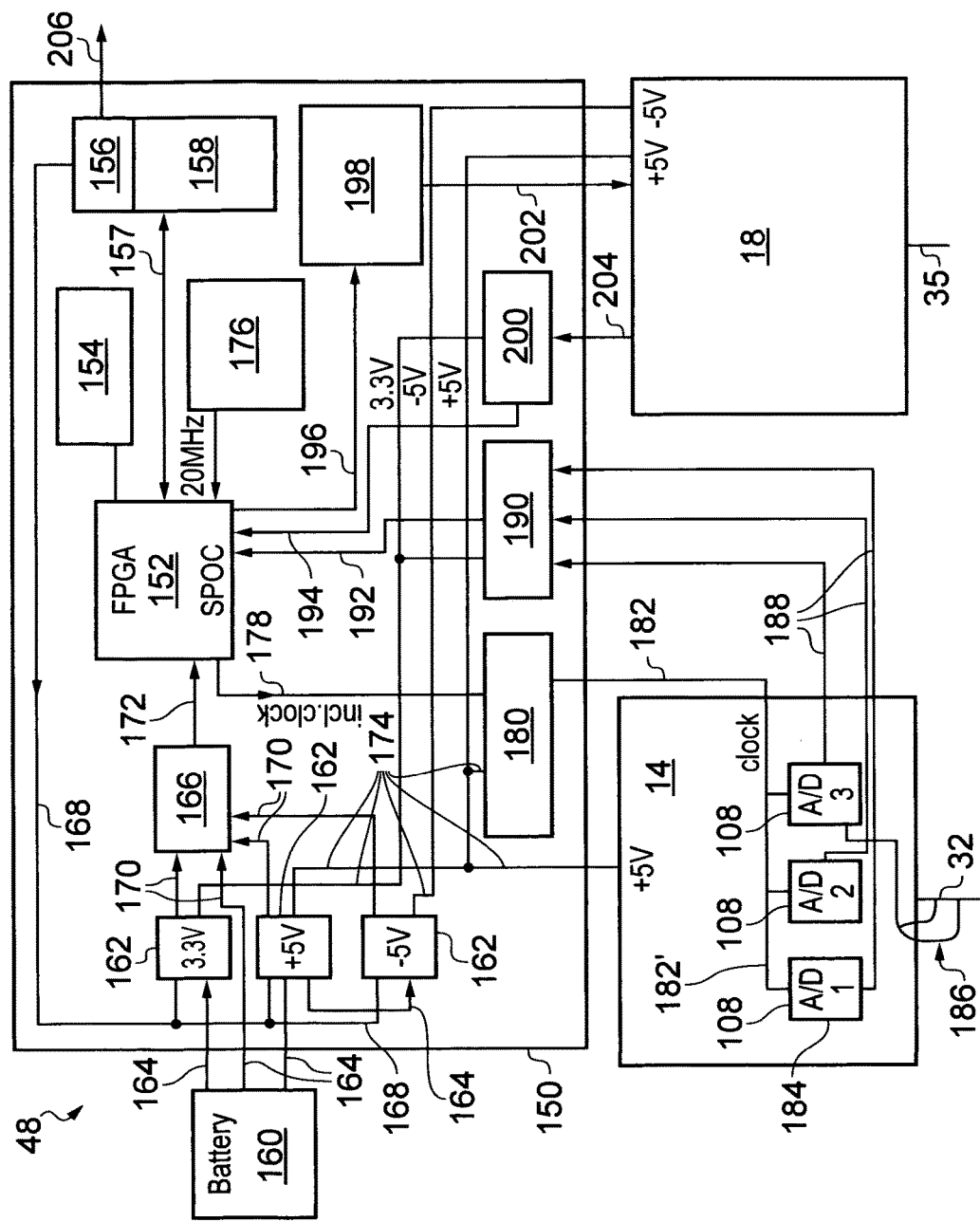
FIG. 13 shows a schematic block diagram of an example data handling module and connections to 2 medical data gathering modules according to an example embodiment of the invention.

FIG. 12 shows a three lead ECG cable 32 having an ECG lead hub 120, ECG connecting lead 122, and ECG cable plug 124. Defibrillation protection in the form of ECG protection circuit 128 up to 5 kV may be provided within ECG lead hub 120 in the three lead and 10 lead ECG cables of FIGS. 11 and 12. FIG. 13 shows a schematic block diagram of a medical data handling module 48 in the form of an FPGA board, in this example an FPGA printed circuit board (PCB) 150. Also shown are ECG interface card 14 and BP interface card 18. A system-programmable-on-a-chip (SPOC) in the form of a field programmable gate array integrated circuit 152 receives instructions in the form of software from an electronically programmable read-only memory 154 (either EEPROM or EPROM may be used although it is preferred that the program is fixed within the medical apparatus during manufacturing at its factory settings). Typically the EEPROM 154 is programmed during manufacturing. Alternative integrated circuits such as microprocessors, ASICS etc may be used in alternative medical data handling modules. The advantage in using an FPGA is that it contains both a central processing unit and memory, and it can be programmed on the fly by an associated separate device such as EEPROM 154 that can be addressed either during manufacturing or by factory based post manufacturing adjustment. EEPROM such as serial flash memory (SFM) may be used.

The FPGA board 150 has an internal interface 158 with a power enable section 156 for enabling power from voltage regulators 162 via power enable line 168 to ECG interface card 14 and BP interface card 18. Internal interface 158 may be a PCI interface e.g. for use in a desktop computer, or an internal USB interface e.g. for use with a laptop computer. Three voltage regulators 162 are provided which deliver 3.3 V, +5 V and −5 V from a battery 160 via battery power in leads 164. A voltage monitor 166 monitors voltage from battery 160 and from each of the three voltage regulators 162 via voltage monitor power input lines 170. Voltage monitor 166 delivers power to FPGA 152 via FPGA power input line 172. ECG interface card 14 and BP Interface card 18 receive regulated voltages via power input lines 174. FPGA 152 delivers control and clock signals via ECG control and clock line 178, data output buffer 180 and data output line 182 to ECG interface card 14. A clock portion 182' of data output line 182 is delivered to three analogue to digital converters 108. Optionally, these then run synchronously saving components and computing time. Thus, in more preferred embodiments of the invention, at least two and, optionally, three analogue to digital converters are provided. Optionally, a three lead/ten lead (and/or lead off) identifier circuit 186 is also provided for identifying whether a three lead or ten lead ECG patient cable is connected to ECG interface card 14 (and/or if no cable is connected). Three ECG data output lines 188 deliver data to ECG data input buffer 190. An ECG data input line 192 then connects to FPGA 152.

A/D converters 108 may sample data at 1 kHz (every 1 ms (millisecond)) or 2 kHz (every 0.5 ms) or at any other suitable sampling rate. FPGA 152 then samples data typically at 1 kHz or 2 kHz or at a suitable sampling rate to provide sufficient data resolution, for example, for any subsequent measurement and calculations that may be required. Thus, in some embodiments, the FPGA 152 may take every other measurement delivered by the A/D converters, in other embodiments it may take every measurement delivered by the A/D converters. In yet further embodiments, the FPGA data collections rate is variable, and/or selected to match the data resolution required by the subsequent medical data measurement and calculation module, which will of course depend upon the nature of the medical data and the measurement or calculation required. For ECG measurements in one embodiment of the invention, the A/D converters collect data every 0.5 ms (at 2 kHz) and the FPGA samples the A/D converters every 1 ms (at 1 kHz)

A BP control line 196 delivers control Instructions to BP control circuit 198 and onward via BP interface control line 202 to BP interface card 18. BP patient cable 35, typically for connecting to a BP cuff 34 (see FIG. 8), is connected to BP interface card 18. Data is sent via BP interface data output line 204 to BP data input buffer 200 and onward to FPGA 152 via BP data input line 194. FPGA connects to FPGA internal data interface 158 via a bidirectional data line 157. FPGA internal data interface 158 connects to internal data bus e.g. USB or PCI (not shown) via line 206. EPROM 154 provides instructions in the form of software to FPGA 152. A clock oscillator 176 provides a clock signal (for example 20 MHz) to FPGA 152.

Figure 14:
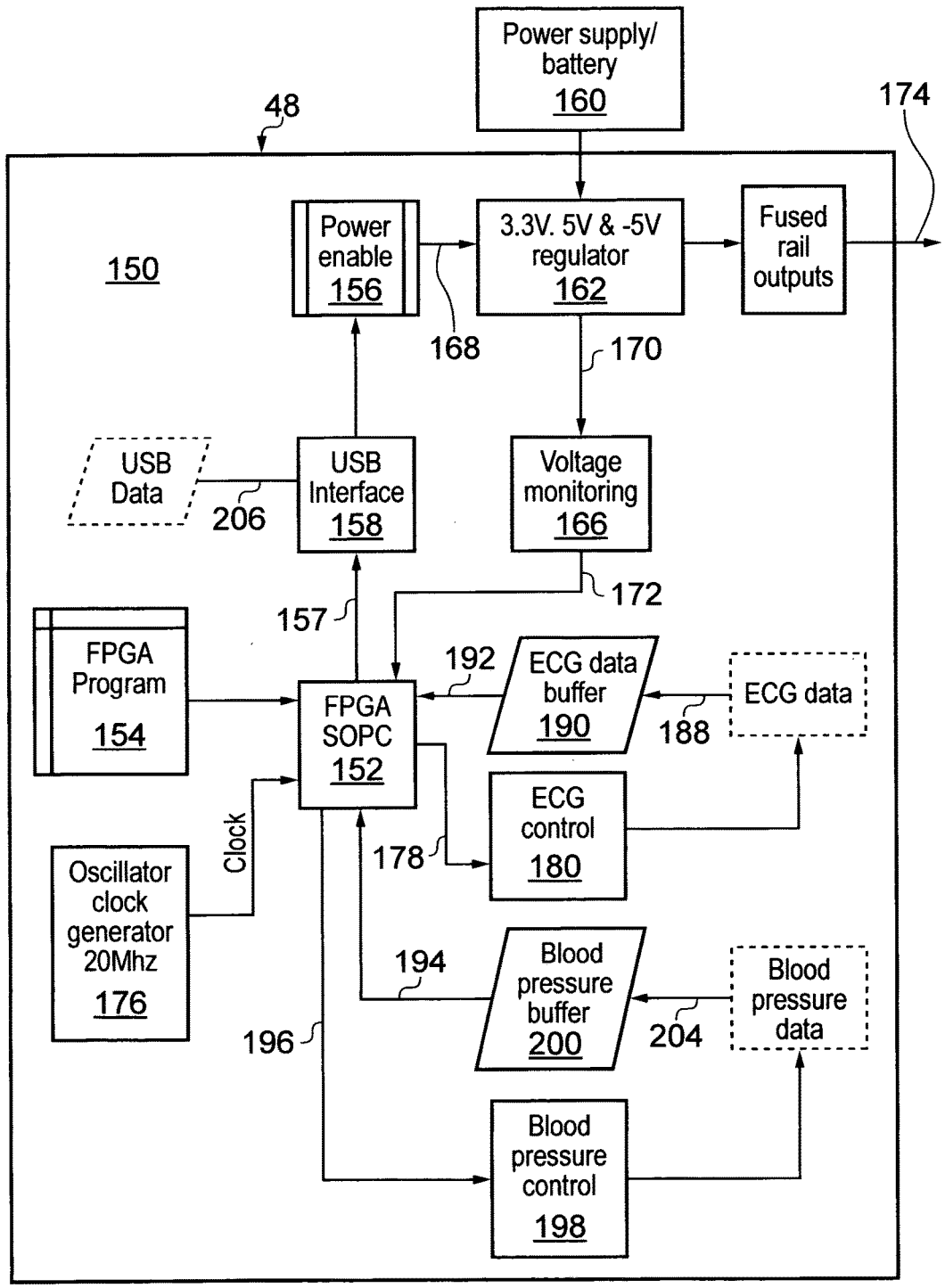
FIG. 14 shows a further schematic block diagram of an example data handling module according to an example embodiment of the invention.

FIG. 14 shows a schematic block diagram of an example data handling module 48 very similar to that shown in FIG. 13. In this example embodiment, data handling module 48 comprises an FPGA interface board 150 for example, in the form of printed circuit board. Also shown are an ECG control module 180 and ECG control lines 178. A battery and/or power supply 160, optionally a medical grade battery and/or a medical grade power supply, is connected via voltage regulators 162, voltage power monitoring lines 170 and FPGA power input/monitoring line 172 to FPGA 152. FPGA 152 provides power enable 156 to voltage regulators 162 via voltage regulator power enable lines 168 and via ECG power input lines 174. In this embodiment, USB data is sent from USB interface 158 via line 206. FPGA program is provided to FPGA 152 from EPROM 154. A clock is provided by oscillator 176. ECG data and BP data is delivered via ECG data input line 188, BP data input line 204, ECG data buffer 190, BP data buffer 200, and data lines 192 and 194 to FPGA microprocessor 152.

Figure 15:
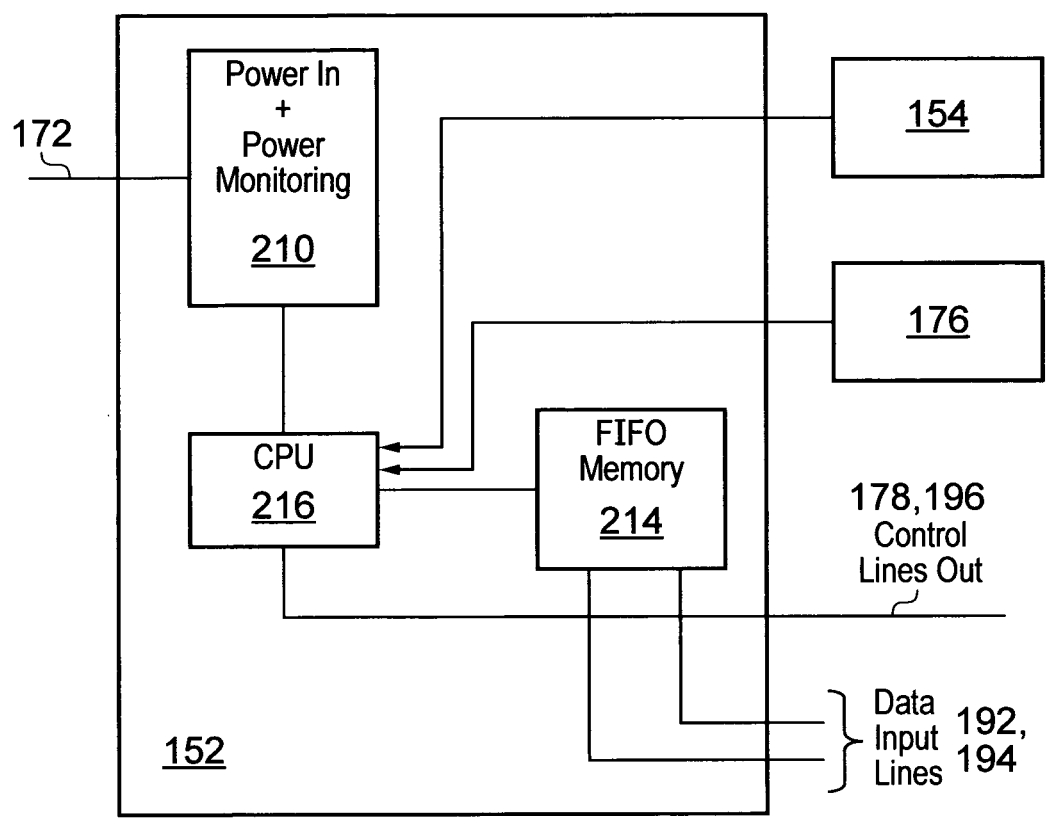
FIG. 15 shows a schematic block diagram of a field programmable gate array (FPGA) and associated electronically programmable read-only memory (EPROM) and clock oscillator according to an example embodiment of the invention.

FIG. 15 is a more detailed schematic view of FPGA microprocessor 152, here in the form of a system on a programmable chip comprising first in first out (FIFO) memory 214 and CPU 216. Power monitoring logic may also be provided (not shown). EPROM 154 is pre-programmed with instructions for CPU 216. Oscillator 176 provides a clock signal to CPU 216. Control lines 178 and 96 are controlled by CPU 216. Data input lines 192, 194 deliver data to FIFO memory 214 upon request by CPU 216.

Figure 16:
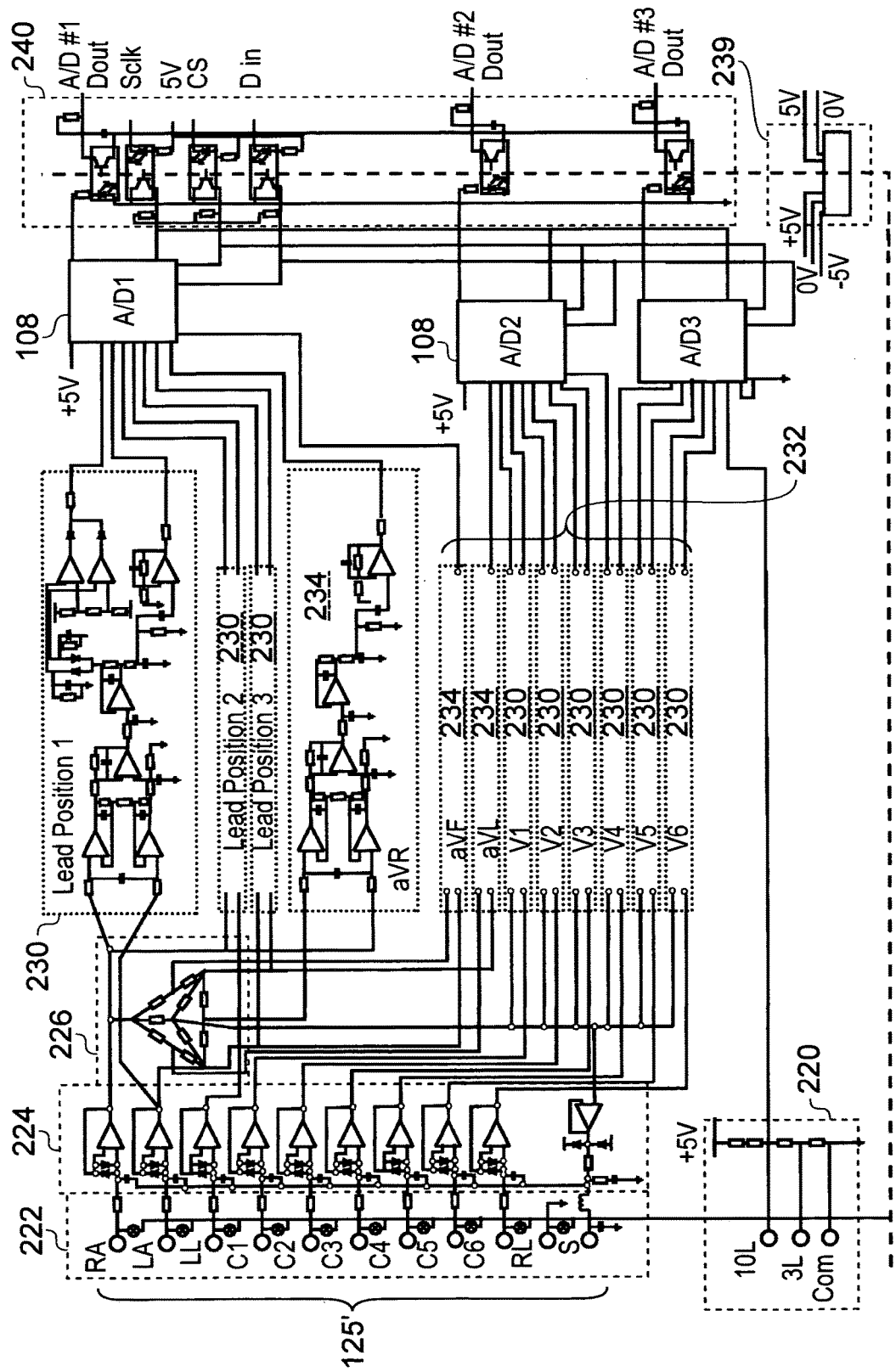
FIG. 16 shows a schematic circuit diagram of a circuit for use in an ECG medical data gathering module according to an example embodiment of the invention.

FIG. 16 shows an example embodiment of an ECG interface circuit comprising patient lead input pins 125', three lead/10 lead identifier circuit 220, defibrillation protection circuits 222, buffer circuit 224, Wilson network circuit 226, ten lead off and amplification circuits 230 optionally including a slew rate limiting circuit (not shown), three amplification circuits 234, three analogue to digital converters 108, power isolation circuit 239 and high-speed optical isolation barrier 240. Thus, optionally, each line from pins 125' has its own amplification circuit, either 230 or 234. Furthermore, two forms of voltage protection are provided in the defibrillation protection circuit 222 and in the high speed optical isolation barrier 240. Alternatively or in addition, voltage protection may also be provided in patient lead 32 (see FIG. 8).

Figure 17:
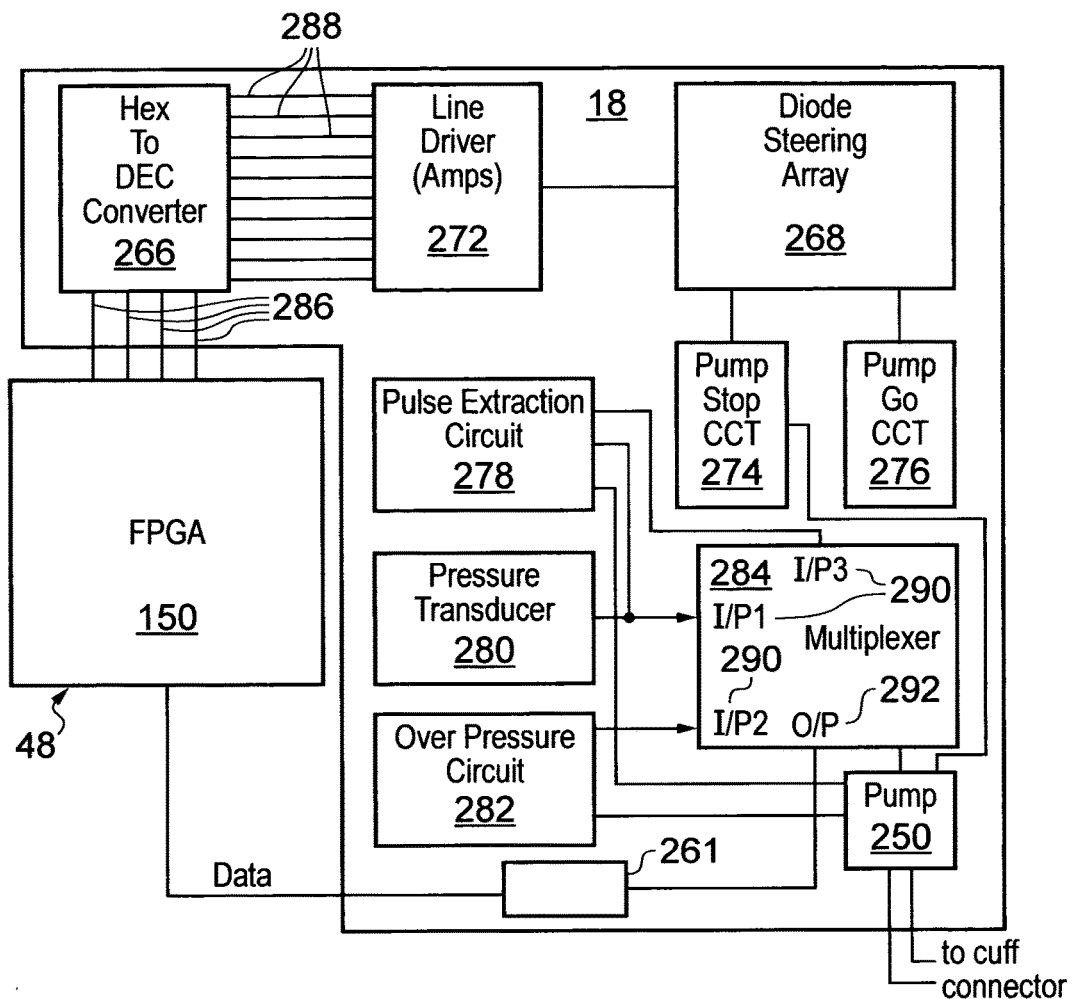
FIG. 17 shows a schematic block diagram of a circuit for use in a BP medical data gathering module according to an example embodiment of the invention.

When identifier circuit 220 shows 2.5V, no patient cable is present. When identifier circuit 220 shows 1.6V, a three lead patient cable is connected. When identifier circuit 220 shows 0V, 10 lead patient cable is connected. FIG. 17 shows a higher level block diagram of a BP interface card 18 and connections to a data handling module in the form of FPGA interface card 150. BP Interface card 18 is connected to a pump 250 mounted thereon (as shown) or adjacent thereto (not shown). BP control lines 286 deliver binary data to hex to decimal converter 266 from FPGA 150. Decimal control lines 288 are connected to line driver amplification 272 and then to diode steering array 268. The diode steering array 268 controls the pump stop circuit 274 and the pump go circuit 276, which in turn control pump 250. Pulse extraction circuit 278, pressure transducer 280 and over pressure transducer 282 collect signals from cuff 34 and deliver these to three inputs 290 of multiplexer circuit 284. Multiplexer circuit 284 has an output 292 that delivers data to medical data handling module 48 (e.g. FPGA 150).

Figure 18:
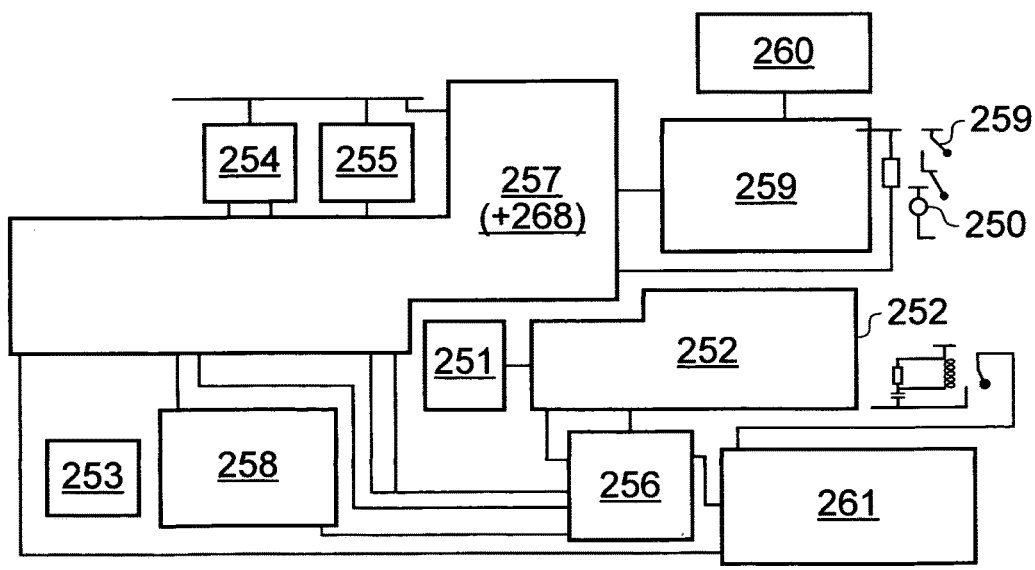
FIG. 18 shows a schematic circuit diagram of an example circuit for use in a BP medical data gathering module according to an example embodiment of the invention.
Figure 19:
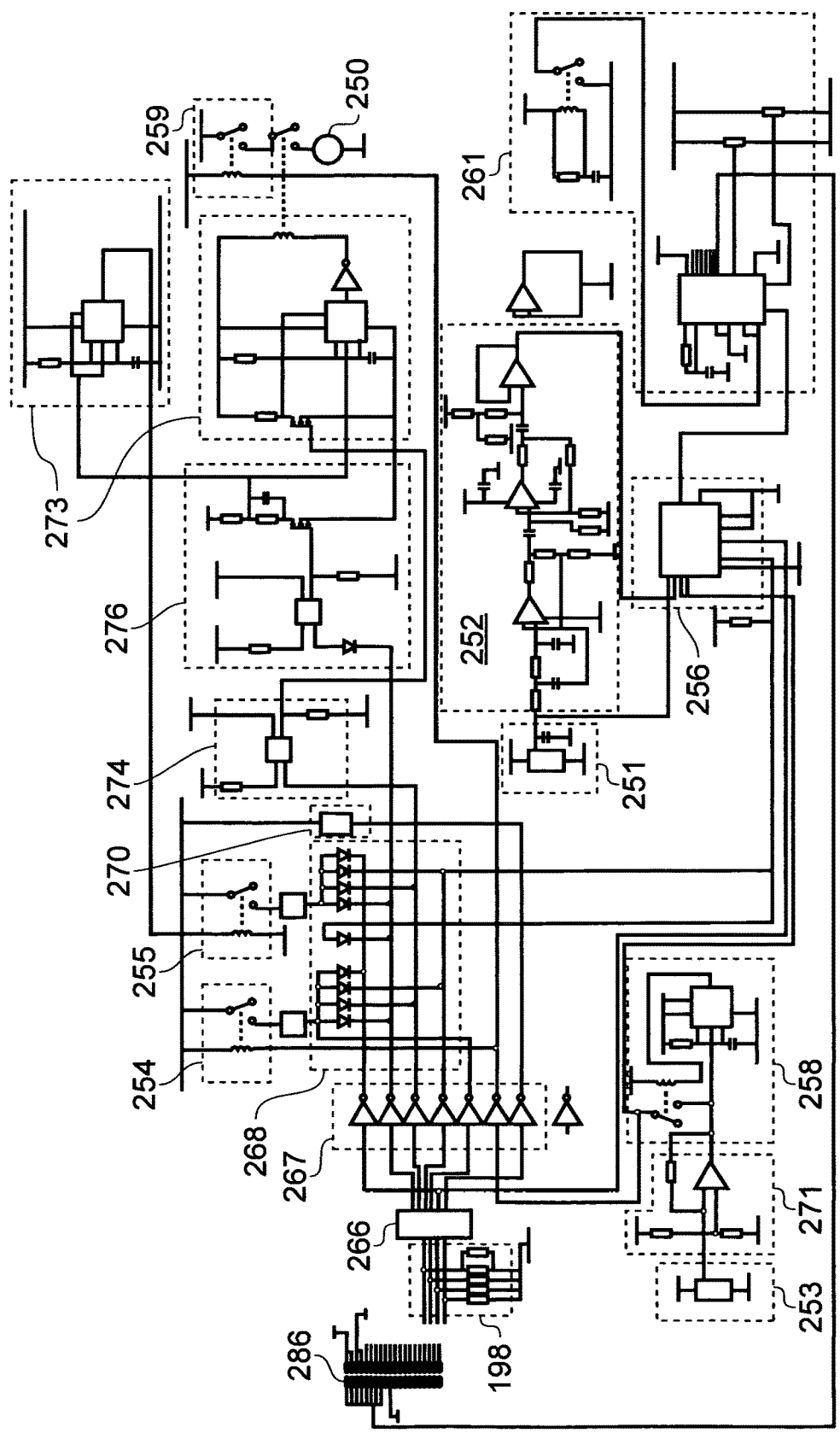
FIG. 19 shows a schematic circuit diagram of an alternative circuit for use in a BP medical data gathering module according to an example embodiment of the invention.

FIGS. 18 and 19 are similar to FIG. 17 but show more detail, in particular these figures show pump 250 for delivering air to a BP cuff 34, a pressure transducer 251, a pulse extraction circuit 252, an over pressure transducer 253 for detecting over pressure, a dump valve 254, a bleed valve 255, a multiplexing circuit 256, a pump control system 257 (including a diode steering array 268—not shown) and an overpressure circuit 258 for detecting and dealing with over pressure, a pump safety circuit 259, an overall timer circuit 260, an analogue to digital converter 261. In FIG. 19, Item 266 is binary (or hex) to decimal converter for converting hex data from the FPGA to a decimal control signal controlling the pump and associated control and measurement circuits. Amplifying line drivers 267 amplify control signals as required. Optionally, each BP input line has its own amplifying line driver 267. A diode steering array 268 controls the pump circuits. Pump control 257 (in FIG. 18) comprises a pump stop 274, a pump go 276, a pump timer and controller 273, a BP control 198, binary to decimal converter 266, line driver 267, sounder 270 and diode steering array 268 (as seen in FIG. 19)

Figure 20:
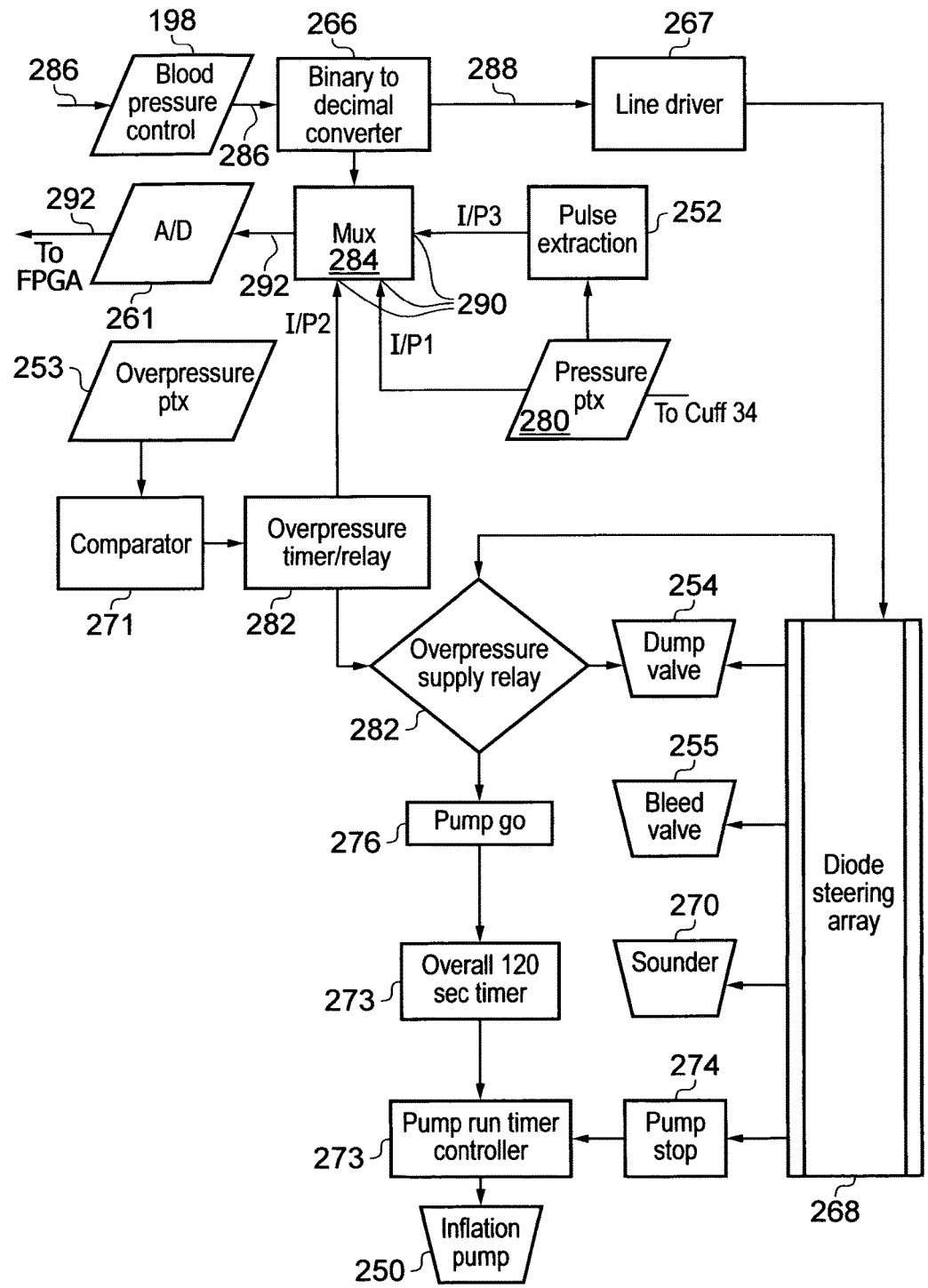
FIG. 20 shows a schematic block diagram of a flow diagram for a BP medical data gathering module according to an example embodiment of the invention.

Turning now to FIG. 20, components and data flow within a BP interface card 18 are shown. Control lines 286 deliver control signals to BP control module 198. Binary to decimal converter 266 converts these to decimal data on decimal BP control lines 288 for amplification by line driver(s) 267. Diode steering array 268 uses these control signals to control dump valve 254, bleed valve 255, sounder 270, pump stop circuit 274, pump go circuit 276, over pressure supply relay and timer circuit 282 and overall control and timer circuits 273. Over pressure transducer 253 delivers signals to over pressure relay via comparators 271. A pulse extraction circuit 252 derives signals from the pressure transducer 280 associated with cuff 34 (see FIG. 8) and both deliver inputs to multiplexer 284. An analogue to digital converter 261 delivers signals to medical data handling module (not shown) from multiplexer 284.

Figures 21A, 21B:
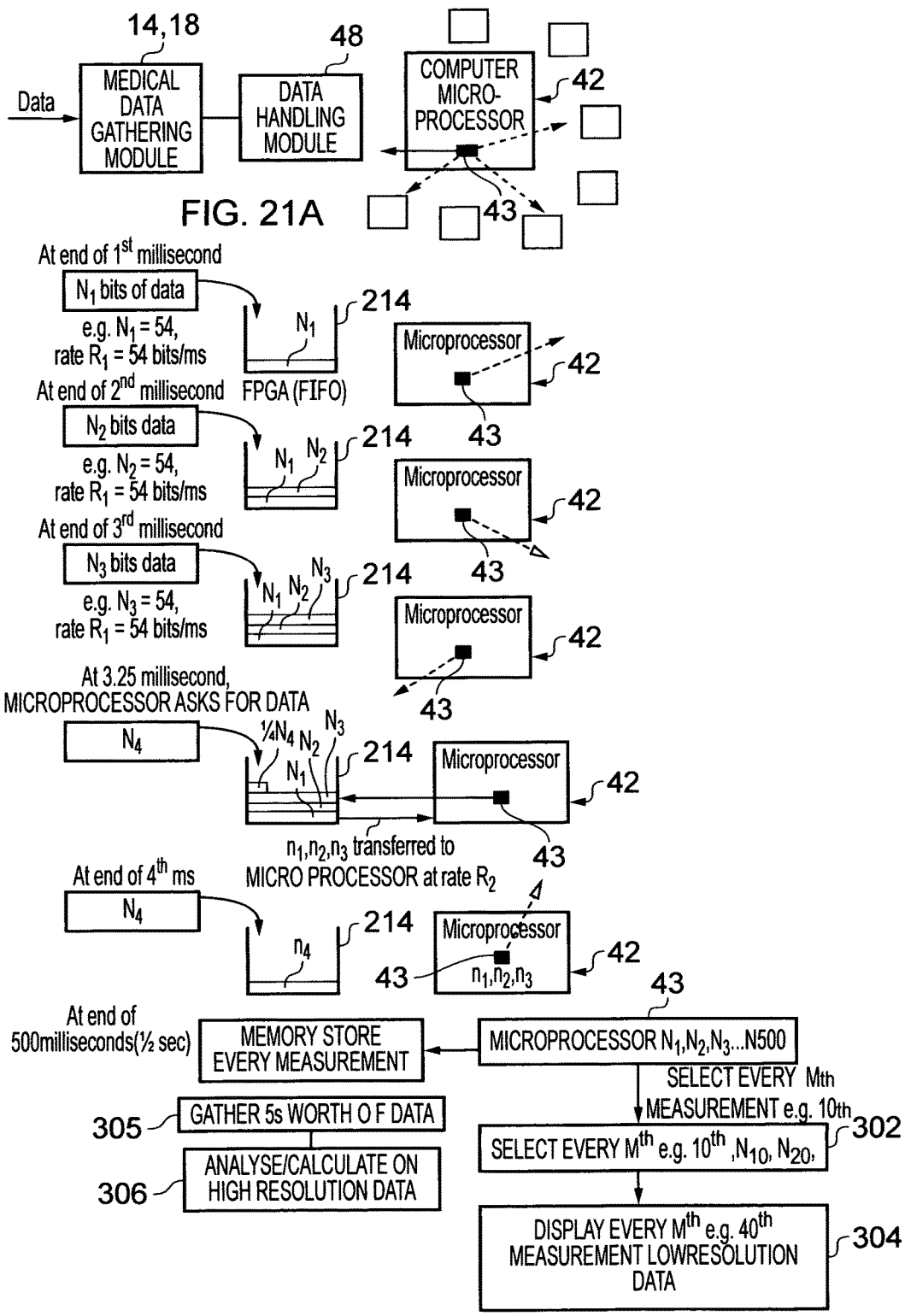
FIG. 21A shows a schematic representation of a medical data gathering module, data handling module and computer including microprocessor and the timing of data transfer therebetween according to an example embodiment of the invention.
FIG. 21B shows a schematic representation of steps taken by the microprocessor in displaying data at a relatively low resolution, and in analysing data at a relatively high resolution according to an example embodiment of the invention.

FIG. 21A shows a schematic representation of medical data gathering modules 14, 18, medical data handling module 48, a computer platform 42 and computer microprocessor 43. At any given point in time, microprocessor 43 may be scheduled or called away to carry out tasks other than retrieving data from the medical data handling module 48. These other tasks are represented by dotted line arrows. Microprocessor 43 has an internal clock, which can operate at up to 3 GHz. However, most operating systems such as Microsoft Windows®, Apple Macintosh® operating systems and Linux operating systems have an internal clock much slower around 20 Hz or 55 ms. By utilising a software clock, such as a system clock loop set to go round enough times to reach 1 ms and counting the loop that number of times, the system/software can be asked to retrieve data from the medical data handling module once every half millisecond or once every millisecond etc. However, as already discussed, the microprocessor 43 has many other tasks to perform such as checking ports etc and cannot reliably be counted upon to retrieve data as scheduled on time, e.g. every millisecond.

The medical data handling module 48 therefore assists the microprocessor 43. Firstly, the medical data handling module 48 samples N bits of data every T1 seconds. In this example T1 equals, 0.25 ms to 10 ms, or 0.5 ms to 5 ms, or 1 ms, or 2 ms. Examples of the medical data sampled is outlined in FIG. 28, which consists here of 54 bits of data from ECG and BP modules and skin temperature measurements. These are split by the A/Ds 108 (see FIGS. 8, 13 and 16) into two parts, namely most significant bit (Msbit) and least significant bit (Lsbit) giving 2×24=48 data bits, plus six BP control and data bits and voltage monitoring data bits are added giving a total of 54 bits. Furthermore, two more bits of USB data for handshaking is added by the FPGA (or by the FPGA user interface) giving a total of 56 bits. Every T1 seconds, in this example every 1 ms, N bits of data are sampled from incoming data lines to the medical data handling module, here a FPGA, and stored in the First In First Out (FIFO) FPGA memory 214. The designation N1, N2, N3 indicates the data were collected in the first, second and third time periods respectively. The predetermined group, here a predetermined number, of data bits collected each time was the same, namely, N. In this example N equals 54. Other quantities of N can be envisaged depending upon the nature and type of medical data being collected. A predetermined group of data may be T1 seconds worth of data.

The microprocessor 43 is programmed to retrieve data from medical data handling module 48, in this case from FPGA 150, every fixed time period T2.

Thus, T2 is the nominal data retrieval request rate. Optionally, and indeed typically, T2 is equal in length to the time period T1 for sampling data. Thus, it may be arranged that T1 equals T2 equals, in this preferred example, 1ms. In this example, then if microprocessor 43 is able to request data from memory 43 every T2 seconds then the FPGA memory 214 is emptied and all data is transferred to microprocessor 43 for analysis and calculation, drawing and display. However, if, as is shown in FIG. 21A, microprocessor is busy for 3 ms and only gets round to retrieving data at $T_{2actual}$ of 3.25 ms (M times×T1 plus a bit), then it retrieves data from the data handling modules in multiples of N (or in multiples of T1 time period's of data) and leaves any remaining data in excess of a multiple of N (or in excess of a T1 time period's worth of data) to be collected in the next data retrieval round.

Interestingly enough, while the data retrieval request rate is T2, typically equal to the data sampling rate of T1, a data retrieval transfer rate is limited only by the capacity of the internal serial bus, typically by the internal USB or PCI bus. Thus, if three lots of multiples of N data bits are transferred and N=54, then the data retrieval transfer rates may be 3×(54+2) per millisecond, whereas, if one lot of N data bits is transferred the data retrieval transfer rates may be 1×(54+2) per millisecond.

Thus, in the above example embodiments, regardless of the microprocessor's ability to clock at 1 ms, or indeed to act upon clocking information every 1 ms to enact a data retrieval round, data sampled at a resolution of T1 seconds (here 1 ms) is stored ready for collection at a later round. This ability to separate the action of the medical data sampling rates (by the medical data handling module 48) and the medical data retrieval request rates (by the microprocessor 43 of computer 2, 22), allows the integration of these components in a single medical apparatus with minimal or no loss of functionality or data resolution, Thus, in this example embodiment, medical data gathering modules, such as ECG and/or BP data gathering modules, can be integrated with a computer motherboard having one or more standard microprocessor and running standard operating system such as Microsoft Windows®, Apple Mac® and Linux operating systems that have limited operating system clock speeds, with minimal risk of losing data resolution, enabling gathering and recording of diagnostic quality grade data.

Turning now to FIG. 21B, data resolution is preserved at the sampling rate required for complex calculations such as heart rate determination or heart rate variability measurements e.g. for diabetic autonomic Neuropathy test (step 300). Typically, these calculations can be commenced once a suitable amount of data is collected e.g., 3 seconds to 40 seconds, or more typically after 5 or 30 seconds of data (step 305). Appropriately high data resolution is necessary for completing accurate calculations of this sort (step 306).

When displaying data, however, such a high level of resolution is not required and, in one example embodiment, drawing modules select every Mth measurement to display and draw this to the screen every K seconds. For example, the Mth measurement may be any of the 5th to 15th measurements and may typically be every $10^{th}$ measurement. Also, for example, K may be from 5 ms to 15 ms and is typically every 10 ms. This can be seen more clearly in FIG. 22.

Figure 22:
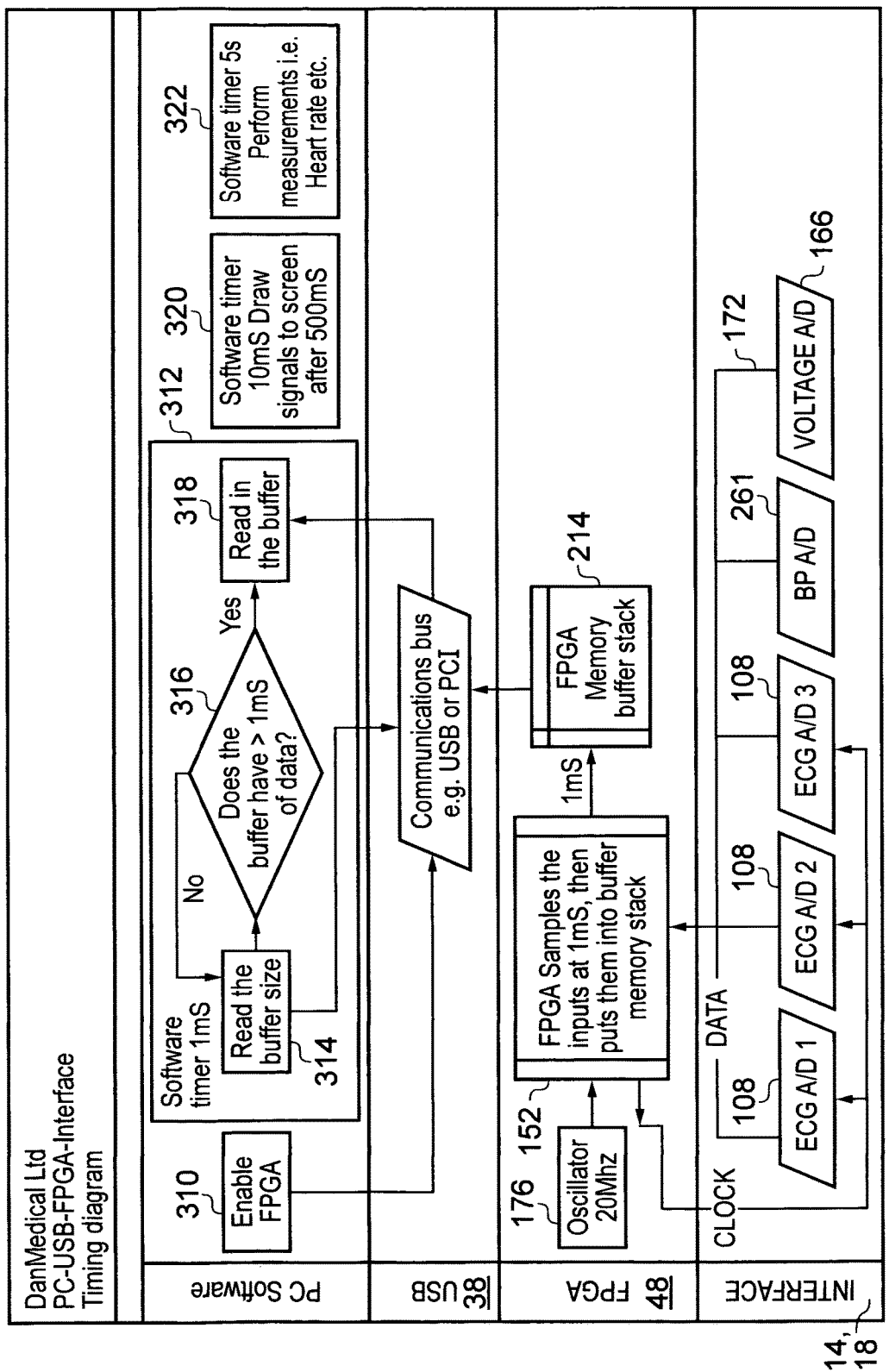
FIG. 22 shows a schematic representation of medical data gathering modules (medical data gathering interfaces such as ECG and BP interfaces), data handling module in the form of an FPGA, a communications interface in the form of a USB, and software running on a PC microprocessor according to an example embodiment of the invention.
Figure 24:
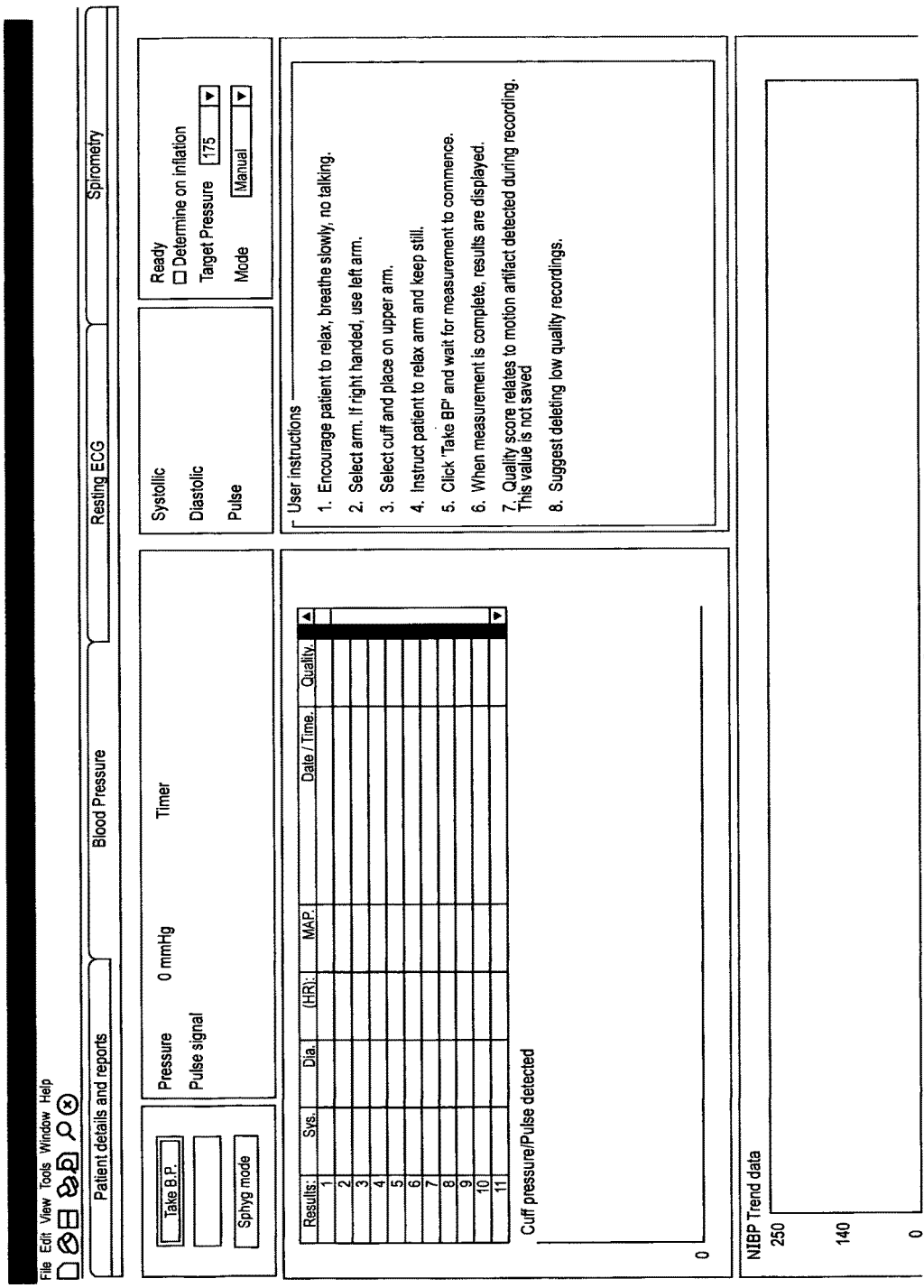
FIG. 24 shows a representation of a user interface screen for use with a blood pressure data gathering module according to an example embodiment of the invention.
Figure 25:
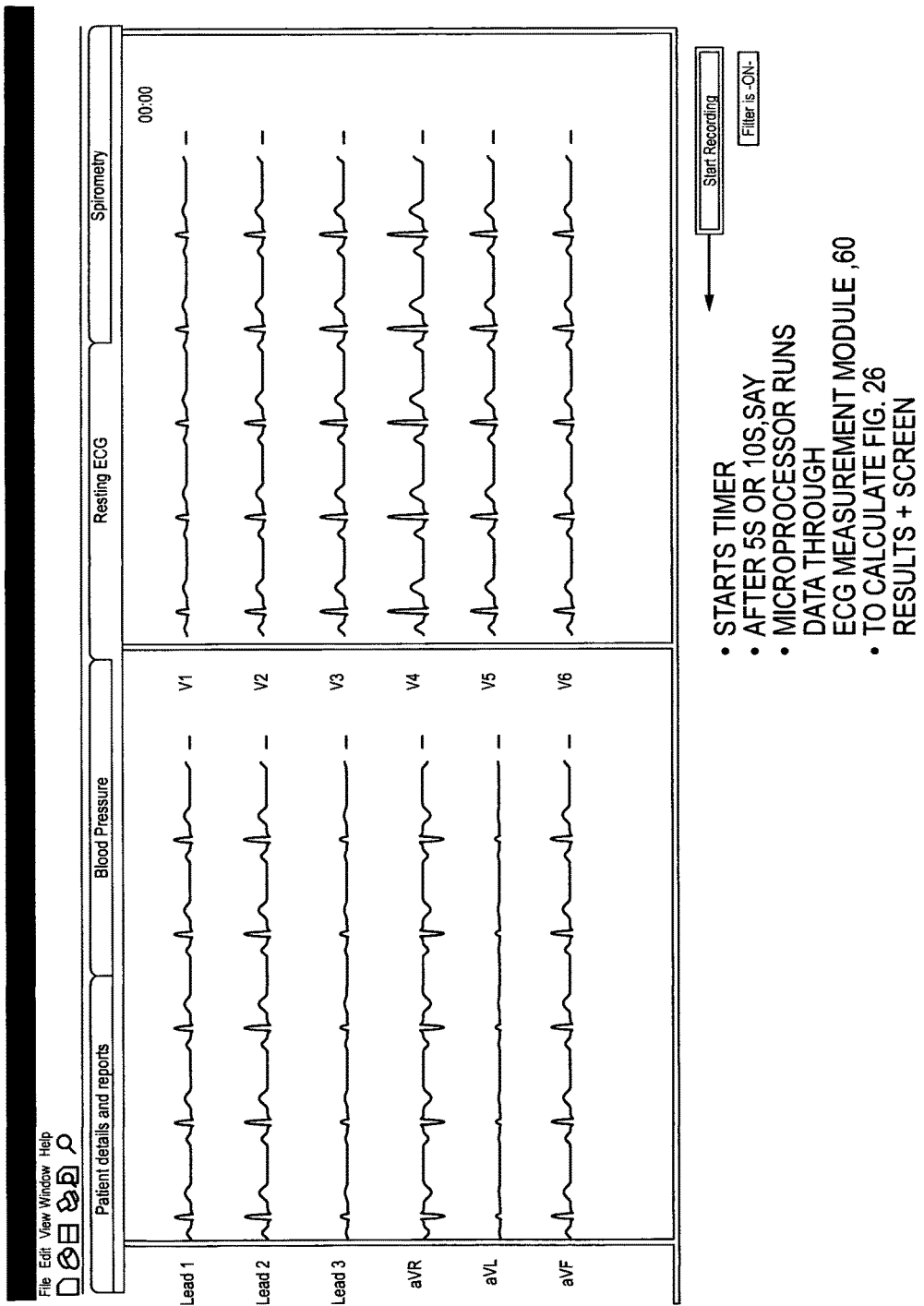
FIGS. 25 and 26 show representations of user interface screens for display of ECG data and calculations in connection therewith, according to an example embodiment of the invention.

In general now in FIG. 22, in step 310, PC software enables the FPGA 152. The PC software reads the buffer size in step 314 and then asks the question does the buffer have more than a given multiple of data, e.g., greater than N bits and/or greater than a given time period's worth of data (e.g. greater than time period T1, here 1 ms), in step 316. If the answer is yes, the microprocessor 43 (not shown) reads the data from the buffer in multiples of N (and/or in multiples of T1 seconds worth of data) in step 318.

In one example, the drawing and display portion of the software draws every $10^{th}$ data points, i.e. the data points from every 10 ms sampling to the screen after 500 ms of data has been collected, in step 320. The drawing step may be carried out every number of seconds, say every K seconds; K may be equal to 2 ms, 5 ms, 10 ms or 20 ms. In step 322, the software performs complex calculations on data signals, e.g. a heart rate etc after five seconds, on the complete data set sampled by the FPGA 150.

Figure 26:
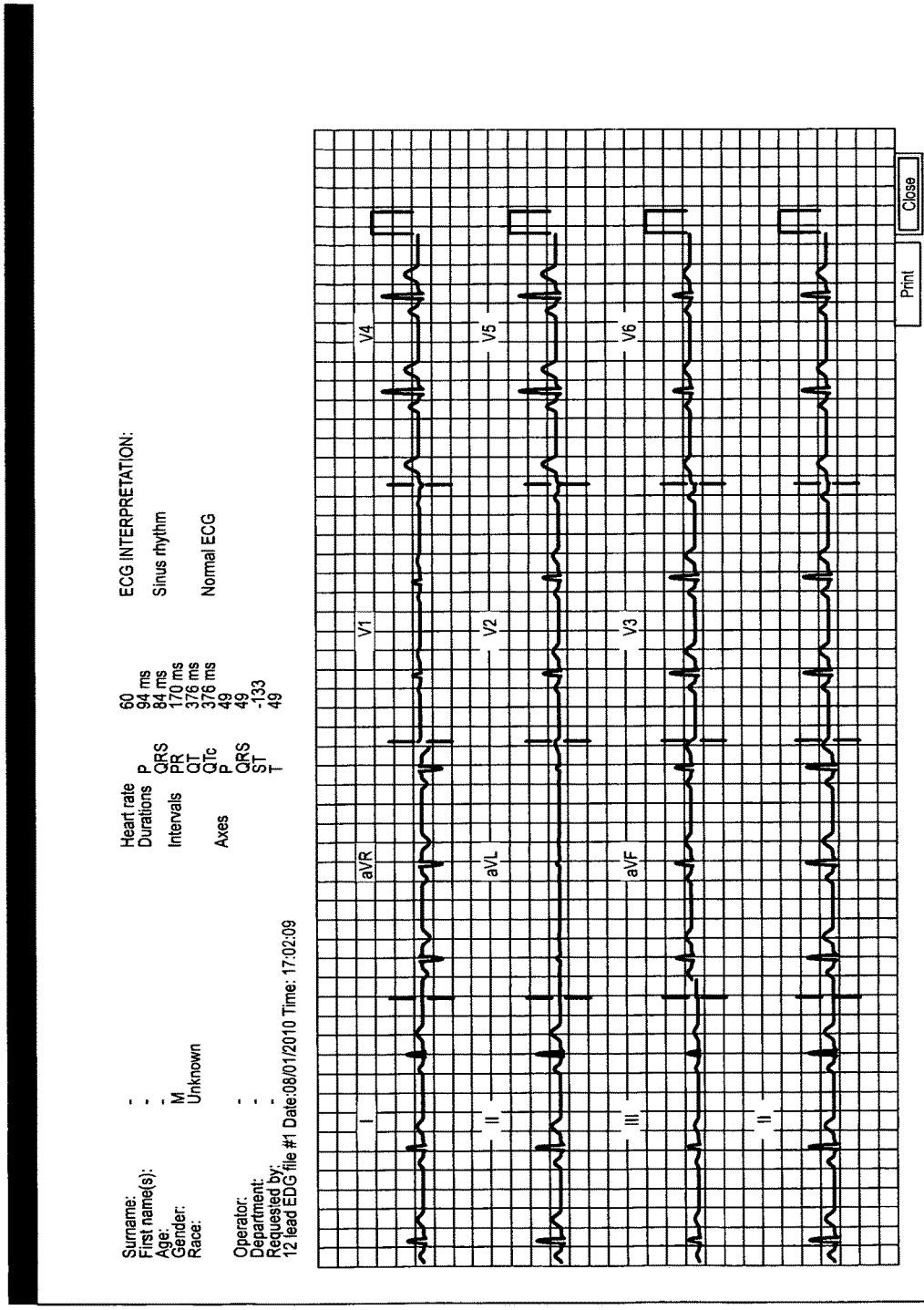

Example data and user interface screens are shown in figure is 23, 24, 25, 26 and 27. FIG. 26 shows results such as durations, intervals, etc calculated on the complete high-resolution data sets at a resolution equivalent to the data sampling rate of the medical data handling module from the medical data gathering modules such as the ECG data gathering module. FIG. 28 shows a table of N data bits where N=54, and ECG, BP and skin temperature are measured. Other examples of medical data gathering modules which could be utilised in this invention individually or in any combination of two or more are electrocardiogram (ECG) signals; blood pressure; invasive or non-invasive blood pressure monitoring; spirometry (lung function); pulse oximetry; temperature; both invasive and non-invasive blood pressure; audiometry testing; retinal testing; dermatology screening (image capture); video endoscopy; video for remote consultations; audio for detection 'Of heart sounds; scaliometer (height); and weighing scales. Thus, one or more of any of these medical data gathering modules may be used in one or more embodiments of the invention.

Whilst specific embodiments of the present invention have been described above, it will be appreciated by those skilled in the art that departures from the described embodiments may still fall within the scope of the present invention.

The invention claimed is:
1. An apparatus for measuring ECG (electrocardiogram) medical data, comprising:
   at least one microprocessor;
   at least one medical data gathering module for gathering ECG medical data, the at least one medical data gathering module comprising a plurality of analogue to digital (A-D) convertors;
   a medical data handling module separate from the at least one microprocessor for buffering the transfer of medical data between the medical data gathering module and the at least one microprocessor, wherein the medical data handling module is arranged to gather and store data in at least one predetermined group of data and the at least one microprocessor is arranged to retrieve data from the medical data handling module in one or more multiples of the at least one predetermined group of data;
   a unitary computer housing, comprising at least one ECG medical data gathering socket for connecting to an ECG cable attachable to a patient and for delivering ECG medical data signals to the at least one medical data gathering module, wherein the at least one medical data gathering module, the at least one microprocessor and the medical data handling module are located within the unitary computer housing;
   a first protection circuit comprising a defibrillation protection circuit at an input to the medical data gathering module, whereby the defibrillation protection circuit protects the medical data gathering module, the medical data handling module, and the microprocessor from defibrillation voltages applied to the patient;
   a second protection circuit comprising an electromagnetic isolation barrier at an output of the medical data gathering module, whereby the electromagnetic isolation barrier protects the patient from voltages from a power supply, and wherein the medical data gathering module lies between the first and second protection circuits so that an analogue ECG medical data signal is amplified and digitised within the medical data gathering module before being processed by the electromagnetic isolation barrier.
2. The apparatus according to claim 1, wherein gathered medical data is retrieved by the at least one microprocessor intermittently from the at least one medical data handling module.

3. The apparatus according to claim 1, wherein the microprocessor comprises Microsoft Windows® or Apple Mac® or Linux operating systems.

4. The apparatus according to claim 1, further comprising a cable identifying circuit for identifying whether a three lead or 10 lead electrocardiogram connecting cable is connected and/or an ECG medical data gathering cable lead off circuit for identifying when no ECG cable is connected.

5. The apparatus according to claim 1, wherein the medical data handling module comprises either 1) a further microprocessor or 2) a further microprocessor and memory or 3) system programmable on a chip or 4) a field programmable gate array (FPGA).

6. The apparatus according to claim 1, wherein the medical data handling module comprises at least one first in first out (FIFO) memory buffer.

7. The apparatus according to claim 1, wherein the medical data handling module comprises either, 1) a programmable read only memory, or 2) an electronically programmable read-only memory (EPROM), or 3) an electronically erasable programmable read only memory (EEPROM), for delivering instructions to the medical data handling module.

8. The apparatus according to claim 1, comprising an internal data bus in which at least one further medical data gathering module is provided and delivers data directly to the at least one microprocessor via the internal data bus.

9. The apparatus according to claim 1, wherein at least one further medical data gathering module is provided, comprising one or more of an electrocardiogram data gathering module, a BP data gathering module, spirometry data gathering module, invasive or non-invasive blood pressure monitoring data gathering module; spirometry (lung function) data gathering module; pulse oximetry data gathering module; temperature data gathering module; both invasive and non-invasive blood pressure data gathering module; audiometry testing data gathering module; audio heart and/or lung sounds data gathering module; retinal testing data gathering module; ultrasound data gathering module; dermatology screening (image capture) data gathering module; imaging, tissue and/or wound care data gathering module; video endoscopy data gathering module; video for remote consultations data gathering module; video conference data gathering module; audio data gathering module; scaliometer (height) data gathering module; foetal heart Doppler ultrasound and/or audio acquisition and/or analysis data gathering module and weighing scales data gathering module.

10. The apparatus according to claim 1, wherein a power supply comprising a rechargeable battery is provided within the housing.

11. The apparatus according to claim 1, comprising an ECG medical data gathering cable.

12. The apparatus according to claim 1, wherein the at least one medical data gathering module gathers data quasi-continuously, and/or at a regular intervals and/or the at least one computer microprocessor retrieves data intermittently and/or or the at least one computer microprocessor retrieves data intermittently either at regular or irregular intervals.

13. The apparatus according to claim 1, wherein the predetermined group of data is N bits of data and/or T1 seconds worth of data and wherein the medical data handling module samples data from the at least one medical data gathering module across N channels once every T1 seconds.

14. The apparatus according to claim 1, wherein the at least one microprocessor attempts to retrieve data in multiples of N bits of data from the data handling module once every T2 seconds and wherein when the at least one microprocessor misses retrieving data the at least one microprocessor attempts to retrieve data in multiples of N from the data handling module at another time and/or at the end of the next T2 second interval.

15. The apparatus according to claim 13, wherein data in excess of a multiple of N and/or of T1 seconds worth of data is left in the medical data handling module until the next data retrieval round.

16. The apparatus according to claim 13, wherein analysis and calculation means is provided for use by the at least one computer microprocessor to conduct analysis and calculation on the medical data at a resolution of T1 seconds, the resolution of the medical data gathering rate.

17. The apparatus according to claim 1, wherein the unitary housing is a unitary laptop computer housing comprising a base, a lid, front wall, rear wall and side walls, and the medical ECG data gathering socket is in one of a front wall, rear wall, side wall.

18. The apparatus according to claim 1, wherein the second protection circuit is provided at the output of the analogue to digital convertors.

19. The apparatus according to claim 1, wherein the analogue to digital convertors receive a common control signal (clock) from the medical data handling module and are set up to run in synchrony.

20. The apparatus according to claim 19, wherein the medical data handling module provides a clock signal to the analogue to digital convertors to control a digitization sampling rate.

21. The apparatus according to claim 1, wherein the medical data handling module collects and stores every measurement delivered by the analogue to digital convertors.

22. A method for measuring ECG medical data, comprising:
providing at least one microprocessor;
providing at least one medical data gathering module for gathering ECG medical data, the at least one medical data gathering module comprising a plurality of analogue to digital (A-D) convertors;
providing a medical data handling module separate from the at least one microprocessor for buffering the transfer of medical data between the medical data gathering module and the at least one microprocessor, wherein the medical data handling module is arranged to gather and store data in at least one predetermined group of data and the at least one microprocessor is arranged to retrieve data from the medical data handling module in one or more multiples of the at least one predetermined group of data;
providing a unitary computer housing, comprising at least one ECG medical data gathering socket for connecting to an ECG cable attachable to a patient and for delivering ECG medical data signals to the at least one medical data gathering module, wherein the at least one medical data gathering module, the at least one microprocessor and the medical data handling module are located within the unitary computer housing;
providing a first protection circuit comprising a defibrillation protection circuit at an input to the medical data gathering module, whereby the defibrillation protection circuit protects the medical data gathering module, the medical data handling module, and the microprocessor from defibrillation voltages applied to the patient;
providing a second protection circuit comprising an electromagnetic isolation barrier at an output of the medical data gathering module, whereby the electromagnetic isolation barrier protects the patient from voltages from a power supply, and wherein the medical data gathering module lies between the first and second protection circuits so that an analogue ECG medical data signal is amplified and digitised within the medical data gathering module before being processed by the electromagnetic isolation barrier; and amplifying and digitising ECG medical data within the medical data gathering module prior to the electromagnetic isolation barrier; and buffering ECG medical data transfer between the medical data gathering module and the microprocessor by the medical data handling module.

23. A method according to claim 22, comprising:

gathering and storing data in predetermined groups of data in the medical data handling module; and, the microprocessor retrieving data from the medical data handling module in one or more multiples of the predetermined groups of data.

24. A method according to claim 22, comprising collecting and storing in the medical data handling module every measurement delivered by the analogue to digital convertors.

* * * * *